US008637709B2

(12) United States Patent
Schaub et al.

(10) Patent No.: US 8,637,709 B2
(45) Date of Patent: Jan. 28, 2014

(54) PROCESS FOR THE PREPARATION OF PRIMARY AMINES BY HOMOGENEOUSLY CATALYZED ALCOHOL AMINATION

(75) Inventors: Thomas Schaub, Neustadt (DE); Boris Buschhaus, Mannheim (DE); Marion Kristina Brinks, Mannheim (DE); Mathias Schelwies, Heidelberg (DE); Rocco Paciello, Bad Duerkheim (DE); Johann-Peter Melder, Boehl-Iggelheim (DE); Martin Merger, Frankenthal (DE)

(73) Assignee: BASF SE, Ludwigshafen (DE)

( * ) Notice: Subject to any disclaimer, the term of this patent is extended or adjusted under 35 U.S.C. 154(b) by 85 days.

(21) Appl. No.: 13/415,174

(22) Filed: Mar. 8, 2012

(65) Prior Publication Data
US 2012/0232309 A1 Sep. 13, 2012

Related U.S. Application Data

(60) Provisional application No. 61/450,161, filed on Mar. 8, 2011.

(51) Int. Cl.
*C07C 209/16* (2006.01)
*C07C 209/18* (2006.01)

(52) U.S. Cl.
USPC ........... 564/480; 564/447; 564/479; 548/565; 548/579; 544/106; 544/358

(58) Field of Classification Search
None
See application file for complete search history.

(56) References Cited

U.S. PATENT DOCUMENTS

| 3,275,554 | A | 9/1966 | Wagenaar |
| 3,708,539 | A | 1/1973 | Fenton |
| 4,709,034 | A | 11/1987 | Marsella |
| 4,756,185 | A | 7/1988 | Shimomura |
| 4,832,702 | A | 5/1989 | Kummer et al. |
| 5,530,127 | A | 6/1996 | Reif et al. |
| 7,754,922 | B2 | 7/2010 | Kubanek et al. |
| 2009/0275781 | A1 | 11/2009 | Kubanek et al. |
| 2010/0022746 | A1 | 1/2010 | Williams |
| 2010/0331573 | A1 | 12/2010 | Schaub et al. |
| 2011/0137029 | A1 | 6/2011 | Kubanek et al. |
| 2011/0137030 | A1 | 6/2011 | Kubanek et al. |
| 2011/0288337 | A1 | 11/2011 | Chedid et al. |
| 2011/0294977 | A1 | 12/2011 | Schaub et al. |
| 2012/0004464 | A1 | 1/2012 | Huyghe et al. |
| 2012/0071692 | A1 | 3/2012 | Ahrens et al. |
| 2012/0095221 | A1 | 4/2012 | Wigbers et al. |
| 2012/0157715 | A1 | 6/2012 | Pape et al. |

FOREIGN PATENT DOCUMENTS

| AU | 2009280778 A1 | 2/2010 |
| DE | 2 125 039 | 12/1971 |
| DE | 36 11 230 A1 | 10/1987 |
| DE | 10 2010 040 427 A1 | 3/2012 |
| EP | 0 234 401 A1 | 9/1987 |
| EP | 0 239 943 A2 | 10/1987 |
| EP | 0 696 572 A1 | 2/1996 |
| WO | WO 03/051508 A1 | 6/2003 |
| WO | WO 2008/006752 A1 | 1/2008 |
| WO | WO 2010/018570 A1 | 2/2010 |
| WO | WO 2011/067199 A1 | 6/2011 |
| WO | WO 2011/067200 A1 | 6/2011 |
| WO | WO 2011/082967 A1 | 7/2011 |
| WO | WO 2011/151268 A1 | 12/2011 |
| WO | WO 2011/157710 A1 | 12/2011 |
| WO | WO 2012/000952 A1 | 1/2012 |
| WO | WO 2012/034933 A1 | 3/2012 |
| WO | WO 2012/049101 A1 | 4/2012 |

OTHER PUBLICATIONS

Imm et al., Angewandte Chemie, International Edition (2010), 49(44), p. 8126-8129.*
U.S. Appl. No. 13/516,521, filed Jun. 15, 2012, Maegerlein, et al.
U.S. Appl. No. 13/158,667, Wigbers, et al.
U.S. Appl. No. 13/415,466, filed Mar. 8, 2012, Schaub, et al.
U.S. Appl. No. 13/415,412, filed Mar. 8, 2012, Schaub, et al.
U.S. Appl. No. 13/415,409, filed Mar. 8, 2012, Schaub, et al.
Yoshihisa Watanabe, et al., "The Ruthenium Catalyzed N-Alkylation and N-Heterocyclization of Aniline Using Alcohols and Aldehydes", Tetrahedron Letters, vol. 22, No. 28, 1981, pp. 2667-2670.
Sebastian Imm, et al., "Selective Ruthenium-Catalyzed Alkylation of Indoles by Using Amines", Chem. Eur. J., 16, DOI:10.1002/chem. 200903261, 2010, pp. 2705-2709.
Annegret Tillack, et al., "A novel ruthenium-catalyzed amination of primary and secondary alcohols", Tetrahedron Letters 47, 2006, pp. 8881-8885.
Dirk Hollmann, et al., "A General Ruthenium-Catalyzed Synthesis of Aromatic Amines", Angew. Chem. Int. Ed., 46, 2007, pp. 8291-8294.
Annegret Tillack, et al., "Salt-Free Synthesis of Tertiary Amines by Ruthenium-Catalyzed Amination of Alcohols", Eur. J. Org. Chem., 2008, pp. 4745-4750.
M. Haniti S. A. Hamid, et al., "Ruthenium-Catalyzed N-Alkylation of Amines and Sulfonamides Using Borrowing Hydrogen Methodology", J. Am. Chem. Soc., 131, 2009, pp. 1766-1774.
Ourida Saidi, at al., "Iridium-catalysed amine alkylation with alcohols in water", Chem. Commun., 46, 2010, pp. 1541-1543.

(Continued)

*Primary Examiner* — Brian J Davis
(74) *Attorney, Agent, or Firm* — Oblon, Spivak, McClelland, Maier & Neustadt, L.L.P.

(57) ABSTRACT

Preparing a primary amine by alcohol amination of alcohol with ammonia and elimination of water includes reacting, in a homogeneously catalyzed reaction, a mixture of alcohol, ammonia, nonpolar solvent, and catalyst, in a liquid phase, to obtain a product mixture. The process then includes phase separating the product mixture into a polar product phase and a nonpolar product phase, and separating off the nonpolar product phase. At least some of the nonpolar phase returns to the homogenously catalyzed reaction. The process further includes separating off amination product from the polar product phase. At least some of the catalyst is in the nonpolar phase, and the catalyst accumulates in the nonpolar phase.

20 Claims, No Drawings

(56) References Cited

OTHER PUBLICATIONS

Natalia Andrushko, et al., "Amination of Aliphatic Alcohols and Diols with an Iridium Pincer Catalyst", ChemCatChem, 2, 2010, pp. 640-643.

K. I. Fujita, et al., "Cp*Ir Complex-Catalyzed Hydrogen Transfer Reactions Directed toward Environmentally Benign Organic Synthesis", Synlett, No. 4, 2005, pp. 560-571.

Alessandro Del Zotto, et al., "Cyclopentadienyl $Ru^{II}$ Complexes as Highly Efficient Catalysts for the N-Methylation of Alkylamines by Methanol", Eur. J. Inorg. Chem., 2004, pp. 524-529.

Ken-ichi Fujita, et al., "N-Alkylation of amines with alcohols catalyzed by a Cp*Ir complex", Tetrahedron Letters 44, 2003, pp. 2687-2690.

Yoshihisa Watanabe, et al., "Ruthenium Complex-Controlled Catalytic N-Mono- or N,N-Dialkylation of Heteroaromatic Amines with Alcohols", J. Org. Chem. 61, 1996, pp. 4214-4218.

Benoit Blank, et al., "An Efficient Method for the Selective Iridium-Catalyzed Monoalkylation of (Hetero)aromatic Amines with Primary Alcohols", Adv. Synth. Catal., 350, 2008, pp. 749-758.

Ana Martinez-Asencio, et al., "N-Alkylation of poor nucleophilic amine and sulfonamide derivatives with alcohols by a hydrogen autotransfer process catalyzed by copper(II) acetate", Tetrahedron Letters 51, 2010, pp. 325-327.

Sebastian Imm, et al., "Eine effiziente und allgemeine Synthese primärer Amine durch Ruthenium-katalysierte Aminierung sekundärer Alkohole mit Ammoniak", Angew. Chem., 122, 2010, pp. 8303-8306.

Dennis Pingen, et al., "Direkte Aminierung von sekundären Alkoholen mit Ammoniak", Angew. Chem., 122, 2010, pp. 8307-8310.

Chidambaram Gunanathan, et al., "Selective Synthesis of Primary Amines Directly from Alcohols and Ammonia", Angew. Chem. Int. Ed., 47, 2008, pp. 8661-8664.

Ryoko Kawahara, et al., "Multialkylation of Aqueous Ammonia with Alcohols Catalyzed by Water-Soluble Cp*Ir-Ammine Complexes", J. Am. Chem. Soc., 132, DOI:10.1021/ja107274w, 2010, 15108-15111.

* cited by examiner

PROCESS FOR THE PREPARATION OF PRIMARY AMINES BY HOMOGENEOUSLY CATALYZED ALCOHOL AMINATION

This patent application claims the benefit of U.S. provisional patent application Ser. No. 61/450,161 filed on Mar. 3, 2011, incorporated in its entirety herein by reference.

The present invention relates to a process for the preparation of primary amines by homogeneously catalyzed alcohol amination of alcohols and alkanolamines with ammonia with the elimination of water in the presence of a complex catalyst which comprises at least one element selected from groups 8, 9 and 10 of the Periodic Table of the Elements and at least one nonpolar solvent.

Primary amines are compounds which have at least one primary amino group (—NH$_2$). Primary diamines have two primary amino groups. Primary triamines have three primary amino groups. Primary polyamines have more than three primary amino groups.

Primary amines are valuable products with a large number of different uses, for example as solvents, stabilizers, for the synthesis of chelating agents, as starting materials for producing synthetic resins, inhibitors, interface-active substances, intermediates in the manufacture of fuel additives (U.S. Pat. No. 3,275,554 A, DE 2125039 A and DE 36 11 230 A), surfactants, drugs and crop protection agents, hardeners for epoxy resins, catalysts for polyurethanes, intermediates for producing quaternary ammonium compounds, plasticizers, corrosion inhibitors, synthetic resins, ion exchangers, textile auxiliaries, dyes, vulcanization accelerators and/or emulsifiers.

Primary diamines and triamines are valuable products with a large number of different uses, for example as solvents, stabilizers, for the synthesis of chelating agents, as starting materials for producing synthetic resins, drugs, inhibitors, corrosion protectants, polyurethanes, as hardeners for epoxy resins, and interface-active substances.

Primary diamines and triamines are currently prepared by heterogeneously catalyzed alcohol amination of primary diols and triols with ammonia. WO 2008/006752 A1 describes a process for the preparation of amines by reacting primary or secondary alcohols with ammonia in the presence of a heterogeneous catalyst which comprises zirconium dioxide and nickel. WO 03/051508 A1 relates to a process for the amination of alcohols using specific heterogeneous Cu/Ni/Zr/Sn catalysts. EP 0 696 572 A1 discloses nickel-, copper-, zirconium- and molybdenum oxide-comprising heterogeneous catalysts for the amination of alcohols with ammonia and hydrogen. According to the documents cited above, the reactions are carried out at temperatures in the range from 150 to 210° C. and ammonia pressures in the range from 30 to 200 bar. However, in the case of the heterogeneously catalyzed processes described in the above documents, the often undesired monoamination products and cyclic amines such as piperazines, pyrrolidines and morpholines are formed as main products. The desired primary diamines are obtained only in extremely low yields, if at all, in the processes described above. The documents cited above describe in particular the reaction of diethylene glycol with ammonia.

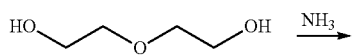

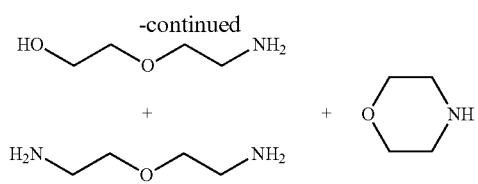

In this process, monoaminodiethylene glycol and morpholine are obtained as main products. The desired diaminated diaminodiethylene glycol is obtained only in extremely low yields, if at all, in the amination reactions of the documents specified above.

The highest yield of diaminodiethylene glycol, at 5%, is obtained according to WO 03/051508 A1, with the formation of 22% morpholine and 36% monoaminodiethylene glycol as by-products.

During the amination of diethanolamine with ammonia, piperazine is obtained as the main product. Here too, the desired linear diamination product diethylenetriamine is only produced in traces if high diethanolamine conversions are operated.

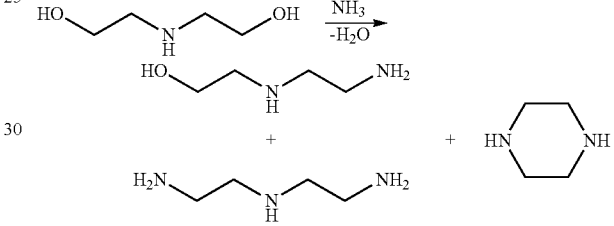

In the case of the reaction of polyetherols to give polyetheramines, with the processes described above, undesired secondary reactions to give the dimeric secondary amine or polymeric coupling product are observed to a high degree on account of the harsh reaction conditions prevailing during the heterogeneously catalyzed amination, as is illustrated below with reference to diethylene glycol. These by-products are difficult to separate off from the desired primary diamination product.

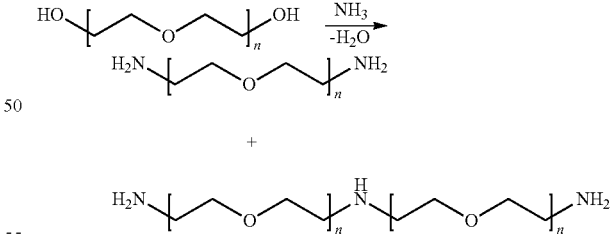

A further problem which is observed during the amination of polyetherols, especially in the case of polyethylene and polypropylene glycol derivatives, is the decomposition of these ethers under the reaction conditions described above since, in particular, the high temperatures and a hydrogen support pressure are required. Under these reaction conditions, gaseous decomposition products are formed which make special safety precautions necessary.

Another disadvantage in the heterogeneous catalysis of the amination of alcohols with ammonia is the high pressures required therefor.

The homogeneously catalyzed amination of alcohols has been known since the 1970s where, in most cases, ruthenium or iridium catalysts are described. Compared with heterogeneously catalyzed reactions, the homogeneously catalyzed amination proceeds at significantly lower temperatures of from 100 to 150° C. The reaction of monoalcohols with primary and secondary amines is described, for example, in the following publications: U.S. Pat. No. 3,708,539; Y. Watanabe, Y. Tsuji, Y. Ohsugi, *Tetrahedron Lett.* 1981, 22, 2667-2670; S. Bähn, S. Imm, K. Mevius, L. Neubert, A. Tillack, J. M. J. Williams, M. Beller, *Chem. Eur. J.* 2010, DOI: 10.1002/chem. 200903144; A. Tillack, D. Hollmann, D. Michalik, M. Beller, *Tetrahedron Lett.* 2006, 47, 8881-8885; D. Hollmann, S. Bähn, A. Tillack, M. Beller, *Angew. Chem. Int. Ed.* 2007, 46, 8291-8294; A. Tillack, D. Hollmann, K. Mevius, D. Michalik, S. Bähn, M. Beller, *Eur. J. Org. Chem.* 2008, 4745-4750; M. H. S. A. Hamid, C. L. Allen, G. W. Lamb, A. C. Maxwell, H. C. Maytum, A. J. A. Watson, J. M. J. Williams, *J. Am. Chem. Soc.* 2009, 131, 1766-1774; O. Saidi, A. J. Blacker, M. M. Farah, S. P. Marsden, J. M. J. Williams, *Chem. Commun.* 2010, 46, 1541-1543; EP 23 9943; N. Andrushko, V. Andrushko, P. Roose, K. Moonen, A. Börner, *ChemCatChem*, 2010, 2, 640-643; K. I. Fujita, R. Yamaguchi, *Synlett*, 2005, 4, 560-571; A. Tillack, D. Hollmann, D. Michalik, M. Beller, *Tet. Lett.* 2006, 47, 8881-8885; A. Del Zlotto, W. Baratta, M. Sandri, G. Verardo, P. Rigo, *Eur. J. Org. Chem.* 2004, 524-529; A. Fujita, Z. Li, N. Ozeki, R. Yamaguchi, *Tetrahedron Lett.* 2003, 44, 2687-2690; Y. Watanabe, Y. Morisaki, T. Kondo, T. Mitsudo *J. Org. Chem.* 1996, 61, 4214-4218, B. Blank, M. Madalska, R. Kempe, *Adv. Synth. Catal.* 2008, 350, 749-750, A. Martinez-Asencio, D. J. Ramon, M. Yus, *Tetrahedron Lett.* 2010, 51, 325-327. The greatest disadvantage of the systems described above is that with these processes only the amination of alcohols with primary and secondary amines is possible. The reaction of alcohols with ammonia to give primary amines, which is the economically most attractive amination reaction, is not described in these works. Neither is any reference made to an efficient recycling of the precious metal catalysts.

The homogeneously catalyzed amination of alcohols with ammonia is only described in a few works. S. Imm, S. Bähn, L. Neubert, H. Neumann, M. Beller, *Angew. Chem.* 2010, 122, 8303-8306 and D. Pingen, C. Müller, D. Vogt, *Angew. Chem.* 2010, 122, 8307-8310 disclose the amination of secondary alcohols such as cyclohexanol with ammonia homogeneously catalyzed with ruthenium catalysts. However, using the systems disclosed therein, it is only possible to aminate secondary alcohols with ammonia. The amination of diols and triols is not described in these works. WO 2010/018570 and C. Gunanathan, D. Milstein, *Angew. Chem. Int. Ed.* 2008, 47, 8661-8664 discloses the amination of primary alcohols with ammonia to give primary monoamines with the help of ruthenium-phosphane complexes. For the amination, specific, acridine-based pincer ligands are used. The reaction is carried out at temperatures of from 110 to 180° C. and $NH_3$ pressures of up to 7.5 bar. Under these conditions, when using primary alcohols, the by-products that are formed are primarily the corresponding imines and dialkylamines. The formation of dialkylamines is especially disadvantageous during the amination of diols since, under these conditions, the cyclic amines are able to form, which likewise fall within the group of secondary amines. The amination of diols and triols with ammonia is not described.

R. Kawahara, K. I. Fujita, R. Yamaguchi, *J. Am. Chem. Soc. DOI:* 10.1021/ja107274w describes the amination of primary monoalcohols and triols with ammonia using an iridium catalyst which has, as ligand, Cp* (1,2,3,4,5-pentamethylcyclopentadienyl) and ammonia. However, using the catalyst system described therein, when reacting primary monoalcohols with ammonia, the undesired tertiary amines are exclusively obtained. The reaction of glycerol with ammonia leads exclusively to the undesired bicyclic quinolizidine.

EP 0 234 401 A1 describes the reaction of diethylene glycol with ammonia in the presence of a ruthenium carbonyl compound. In the process described in EP 0 234 401 A1, only the monoamination product (monoethanolamine), the secondary and tertiary amines (di- and triethanolamine) and cyclic products (N-(hydroxyethyl)piperazine and N,N'-bis(hydroxyethyl)piperazine) are formed. The desired 1,2-diaminoethane is not obtained in this process.

All of the processes described above for the reaction of alcohols with ammonia have the disadvantage that the desired primary amines are not formed as the main products. Moreover, no concepts for recycling the expensive precious metal catalysts are described, although this is required for an industrial transfer of these processes for reasons of cost.

It is an object of the present invention to provide a process for the preparation of primary amines by alcohol amination of mono-, di-, tri- and polyols, and also of alkanolamines with the favorable aminating agent ammonia, in which the catalyst used can be separated off and reused. The reaction should proceed under milder conditions and produce higher selectivities with regard to the formation of primary amines than the established, heterogeneously catalytic reactions. In particular, the selectivity in the preparation of linear primary amines, and also the selectivity in the preparation of di-, tri- and polyamines should be improved.

According to the invention, this object is achieved by the following process for the preparation of primary amines by alcohol amination of alcohols with ammonia with the elimination of water, comprising the steps (a) homogeneously catalyzed reaction of a reaction mixture comprising at least one alcohol, ammonia, at least one nonpolar solvent and at least one catalyst comprising at least one element selected from groups 8, 9 and 10 of the Periodic Table of the Elements in the liquid phase, giving a product mixture (P), (b) phase separation of the product mixture (P) obtained in step (a), optionally after lowering the temperature, lowering the pressure and/or adding at least one polar solvent which has a miscibility gap with the nonpolar solvent, to give at least one polar product phase (A) and at least one nonpolar phase (B) comprising at least some of the catalyst used and separating off the nonpolar phase (B), (c) returning at least some of the nonpolar phase (B) to the reaction in step (a) and (d) separating off the amination product from the polar product phase (A), where the nonpolar solvent used in (a) and the catalyst used in step (a) are selected such that the catalyst accumulates in the nonpolar phase (B).

Surprisingly, it has been found that with the complex catalysts used in the process according to the invention which comprise at least one element selected from group 8, 9 and 10 of the Periodic Table of the Elements, it is possible to obtain primary amines, preferably di-, tri- and polyamines, and also alkanolamines by the homogeneously catalyzed amination of alcohols with ammonia with the elimination of water. The process according to the invention has the advantage that it produces primary mono-, di-, tri- and polyamines and also alkanolamines in considerably improved yields compared with the processes described in the prior art. Moreover, the formation of undesired by-products such as secondary and tertiary amines and also cyclic amines is reduced compared with the prior art. Through appropriate choice of the catalyst and the solvent used, after the reaction, a liquid two-phase system is obtained in which the catalyst accumulates preferentially in the nonpolar phase and the amination product accumulates preferentially in the polar phase, meaning that the catalyst can be easily separated off from the product phase with the nonpolar phase and be reutilized.

Starting Materials

In the process according to the invention, alcohols which have at least one OH group, preferably in the form of the functional group of the formula (—$CH_2$—OH) (primary alcohol group) or (>CH—OH) (secondary alcohol group), are used as starting materials. Preferably, the alcohols have at least one further functional group (—X), where (—X) is selected from hydroxyl groups (—OH) and primary amino groups (—$NH_2$). In this connection, in the process according to the invention, particular preference is given to using starting materials in which (—X) is selected from the group of functional groups of the formulae (—$CH_2$—OH) and (>CH—OH) and (—$CH_2$—$NH_2$) and (>CH—$NH_2$). The starting materials then have at least one functional unit of the formula (—OH), preferably of the formula (—$CH_2$—OH) and (>$CH_2$—OH) and/or at least one further functional group selected from the group of functional groups of the formula (—$CH_2$—OH) and (>$CH_2$—OH) and (—$CH_2$—$NH_2$) and (>$CH_2$—$NH_2$). According to the invention, very particular preference is given to using the starting materials described above which, when reacted with $NH_3$, produce linear primary amines, and very particular preference is given to using linear diols which have at least 2 OH groups, i.e. have two primary and/or secondary alcohol groups, and also linear alkanolamines which have at least one primary or secondary alcohol group in the form of (—$CH_2$—OH) or (>CH—OH).

Suitable starting materials are practically all alcohols which satisfy the prerequisites specified above. The alcohols may be linear, branched or cyclic, preferably linear. Moreover, the alcohols can carry substituents which exhibit inert behavior under the reaction conditions of the alcohol amination, for example alkoxy, alkenyloxy, alkylamino, dialkylamino and halogen (F, Cl, Br, I).

Suitable starting materials which can be used in the process according to the invention are, for example, monoalcohols, diols, triols, polyols and alkanolamines which have at least one OH group, preferably in the form of the functional groups of the formula (—$CH_2$—OH) or (>CH—OH) and at least one further functional group (—X), where (—X) is selected from hydroxyl groups and primary amino groups.

Moreover, diols, triols, polyols and alkanolamines which have at least one OH group and at least one further functional primary or secondary OH unit or $NH_2$ unit are suitable.

Starting materials which can be used are all known diols which have at least one primary or secondary OH group. Examples of diols which can be used as starting materials in the process according to the invention are 1,2-ethanediol (ethylene glycol), 1,2-propanediol (1,2-propylene glycol), 1,3-propandiol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 2,4-dimethyl-2,5-hexanediol, hydroxypivalic acid neopentyl glycol ester, diethylene glycol, triethylene glycol, 2-butene-1,4-diol, 2-butyne-1,4-diol, poylethylene glycols, polypropylene glycols, such as 1,2-polypropylene glycol and 1,3 polypropylene glycol, polytetrahydrofuran, diethanolamine, 1,4-bis-(2-hydroxyethyl)piperazine, diisopropanolamine, N-butyldiethanolamine, 1,10-decanediol, 1,12-dodecanediol, 2,5-(dimethanol)-furan, 1,4-bis(hydroxymethyl)cyclohexane, C36-diol (mixture of isomers of alcohols of the empirical formula ($C_{36}H_{74}O_2$)) and N-methyldiethanolamine, isosorbide (1,4:3,6-dianhydroglucitol), isomannitol (1,4:3,6-dianhydromannitol, diisopropanol-p-toluidine, N,N-di(2-hydroxyethyl)anilines, diisopropanolamine.

Preference is given to diols which have two functional groups of the formula (—$CH_2$—OH).

Particularly preferred diols are 1,2-ethanediol (ethylene glycol), 1,2-propanediol (1,2-propylene glycol), 1,3-propanediol (1,3-propylene glycol), 1,4-butanediol (1,4-butylene glycol), 2-methyl-1,3-propanediol, 2,2-dimethyl-1,3-propanediol (neopentyl glycol), 1,5-pentanediol, 1,6-hexanediol, 1,7-heptanediol, 1,8-octanediol, 1,9-nonanediol, diethylene glycol, triethylene glycol, polyethylene glycols, polypropylene glycols, such as 1,2-polypropylene glycol and 1,3 polypropylene glycol, polytetrahydrofuran, diethanolamine, diisopropanolamine, N-butyldiethanolamine, 2,5-(dimethanol)-furan and N-methyldiethanolamine.

All known triols can be used as starting materials, preference being given to triols which have at least one functional group of the formula (—$CH_2$—OH) or (>CH—OH), and particular preference being given to triols with at least two functional groups of the formula (—$CH_2$—OH) or (>CH—OH). Examples of triols which can be used as starting materials in the process according to the invention are glycerol, trimethylolpropane, triisopropanolamine and triethanolamine.

Particularly preferred triols are glycerol, trimethylolpropane and triethanolamine.

All known polyols can be used as starting materials; these preferably comprise at least one functional group of the formula (—$CH_2$—OH) or (>CH—OH). Examples of polyols which can be used as starting materials in the process according to the invention are polyvinylalcohol, 2,2-bis(hydroxymethyl)-1,3-propanediol (pentaerythritol), sorbitol, inositol, sugars and polymers such as, for example, glucose, mannose, fructose, ribose, deoxyribose, galactose, N-acetylglucosamine, fucose, rhamnose, sucrose, lactose, cellobiose, maltose and amylose, cellulose, starch and xanthan.

Preference is given to polyols which have at least two functional groups of the formula (—$CH_2$—OH) or (>CH—OH).

Particularly preferred polyols are glucose and cellulose.

Starting materials which can be used are also all known alkanolamines which have at least one OH group, preferably a primary or secondary hydroxyl group and at least one primary amino group (—$NH_2$). Within the context of the invention, the alkanolamines are included among the alcohols to be used as starting materials. Examples of alkanol-amines which can be used as starting materials in the process according to the invention are monoaminoethanol, 3-aminopropan-1-ol, 2-aminopropan-1-ol, 4-aminobutan-1-ol, 2-aminobutan-1-ol, 3-aminobutan-1-ol, 5-aminopentan-1-ol, 2-aminopentan-1-ol, 6-aminohexan-1-ol, 2-aminohexan-1-ol, 7-aminoheptan-1-ol, 2-aminoheptan-1-ol, 8-aminooctan-1-ol, 2-aminooctan-1-ol, N-(2-hydroxyethyl)aniline, 2-(2-aminoethoxy)ethanol, N-(2-hydroxyethyl)-1,3-propanediamine and aminodiethylene glycol (2-(2-aminoethoxy)ethanol).

Preference is given to alkanolamines which have at least one primary hydroxyl group (—$CH_2$—OH) and at least one primary amino group of the formula (—$CH_2$—$NH_2$).

Particularly preferred alkanolamines are monoaminoethanol, 3-aminopropan-1-ol, 2-aminopropan-1-ol, 4-aminobutan-1-ol and 2-(2-aminoethoxy)ethanol.

Complex Catalyst

The process according to the invention uses at least one complex catalyst which comprises at least one element selected from groups 8, 9 and 10 of the Periodic Table of the Elements (nomenclature in accordance with IUPAC). The elements of group 8, 9 and 10 of the Periodic Table of the Elements comprise iron, cobalt, nickel, ruthenium, rhodium, palladium, osmium, iridium and platinum. Preference is given to complex catalysts which comprise at least one element selected from ruthenium and iridium.

The complex catalyst comprises preferably at least one donor ligand, in particular one phosphorus donor ligand. The complex catalyst particularly preferably comprises at least one element selected from ruthenium and iridium and at least one phosphorus donor ligand.

In one embodiment, the process according to the invention is carried out in the presence of at least one complex catalyst of the general formula (I):

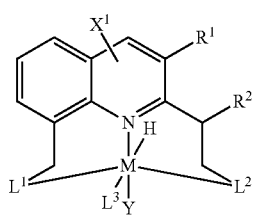

(I)

in which $L^1$ and $L^2$ independently of one another, are phosphine ($PR^aR^b$), amine ($NR^aR^b$), sulfide, SH, sulfoxide (S(=O)R), $C_5$-$C_{10}$-heteroaryl comprising at least one heteroatom selected from nitrogen (N), oxygen (O) and sulfur (S), arsine ($AsR^aR^b$), stibane ($SbR^aR^b$) or N-heterocyclic carbenes of the formula (II) or (III):

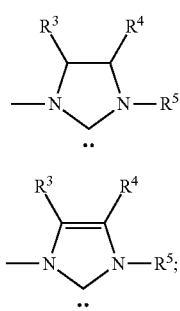

$L^3$ is a monodentate two-electron donor selected from the group carbon monoxide (CO), $PR^aR^bR^c$, $NO^+$, $AsR^aR^bR^c$, $SbR^aR^bR^c$, $SR^aR^b$, nitrile (RCN), isonitrile (RNC), nitrogen ($N_2$), phosphorus trifluoride ($PF_3$), carbon monosulfide (CS), pyridine, thiophene, tetrahydrothiophene and N-heterocyclic carbenes of the formula (II) or (III);

$R^1$ and $R^2$ are both hydrogen or, together with the carbon atoms to which they are bonded, are a phenyl ring which, together with the quinolinyl unit of the formula (I), forms an acridinyl unit;

R, $R^a$, $R^b$, $R^c$, $R^3$, $R^4$, and $R^5$, independently of one another, are unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

Y is monoanionic ligand selected from the group H, F, Cl, Br, I, OCOR, $OCOCF_3$, $OSO_2R$, $OSO_2CF_3$, CN, OH, OR and $N(R)_2$ or neutral molecule selected from the group $NH_3$, $N(R)_3$ and $R_2NSO_2R$;

$X^1$ is one, two, three, four, five, six or seven substituents on one or more atoms of the acridinyl unit or one, two, three, four or five substituents on one or more atoms of the quinolinyl unit, where $X^1$, independently of the others, is selected from the group consisting of hydrogen, F, Cl, Br, I, OH, $NH_2$, $NO_2$, —NC(O)R, C(O)$NR_2$, —OC(O)R, —C(O)OR, CN and borane derivatives which are obtainable from the catalyst of the formula (I) by reaction with $NaBH_4$, and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl and $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl; and M is iron, cobalt, nickel, ruthenium, rhodium, palladium, osmium, iridium or platinum.

Here, it is to be noted that the complex catalyst of the formula (I) for cases where Y is a neutral molecule from the group $NH_3$, $NR_3$, $R_2NSO_2R$, carries a positive charge.

In a preferred embodiment, the process according to the invention is carried out in the presence of at least one homogeneously dissolved complex catalyst of the formula (I), where the substituents have the following meaning:

$L^1$ and $L^2$, independently of one another, are $PR^aR^b$, $NR^aR^b$, sulfide, SH, S(=O)R, $C_5$-$C_{10}$-heteroaryl comprising at least one heteroatom selected from N, O and S;

$L^3$ is a monodentate two-electron donor selected from the group CO, $PR^aR^bR^c$, $NO^+$, RCN, RNC, $N_2$, $PF_3$, CS, pyridine, thiophene and tetrahydrothiophene;

$R^1$ and $R^2$ are both hydrogen or, together with the carbon atoms to which they are bonded, are a phenyl ring which, together with the quinolinyl unit of the formula (I), forms an acridinyl unit;

R, $R^a$, $R^b$, $R^c$, $R^3$, $R^4$, and $R^5$, independently of one another, are unsubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl or $C_5$-$C_{10}$-heteroaryl comprising at least one heteroatom selected from N, O and S;

Y is monoanionic ligand selected from the group H, F, Cl, Br, OCOR, $OCOCF_3$, $OSO_2R$, $OSO_2CF_3$, CN, OH, OR or $N(R)_2$;

$X^1$ is one, two, three, four, five, six or seven substituents on one or more atoms of the acridinyl unit or one, two, three, four or five substituents on one or more atoms of the quinolinyl unit, where $X^1$, independently of the others, is selected from the group consisting of hydrogen, F, Cl, Br, I, OH, $NH_2$, $NO_2$, —NC(O)R, C(O)$NR_2$, —OC(O)R, —C(O)OR, CN and borane derivatives which are obtainable from the catalyst of the formula (I) by reaction with NaBH$_4$, and unsubstituted C$_1$-C$_{10}$-alkoxy, C$_1$-C$_{10}$-alkyl, C$_3$-C$_{10}$-cycloalkyl, C$_3$-C$_{10}$-heterocyclyl comprising at least one heteroatom selected from N, O and S, C$_5$-C$_{10}$-aryl and C$_5$-C$_{10}$-heteroaryl comprising at least one heteroatom selected from N, O and S;

and

M is ruthenium or iridium.

In a further preferred embodiment, the process according to the invention is carried out in the presence of at least one homogeneously dissolved complex catalyst, where R$^1$ and R$^2$ are both hydrogen and the complex catalyst is a catalyst of the formula (IV):

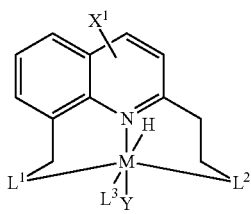

(IV)

and X$^1$, L$^1$, L$^2$, L$^3$ and Y have the meanings given above.

In a further preferred embodiment, the process according to the invention is carried out in the presence of at least one homogeneously dissolved complex catalyst, where R$^1$ and R$^2$, together with the carbon atoms to which they are bonded, form a phenyl ring which, together with the quinolinyl unit of the formula (I), forms an acridinyl unit and the complex catalyst is a catalyst of the formula (V):

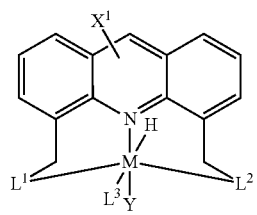

(V)

and X$^1$, L$^1$, L$^2$, L$^3$ and Y have the meanings given above.

By way of example, a number of complex catalysts (formulae (VI), (VII), (VIII), (IX), (X), (XI), (XII) and (XIII)) which can be used in the process according to the invention are listed below:

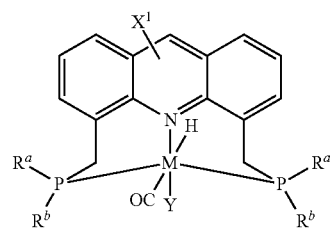

(VI)

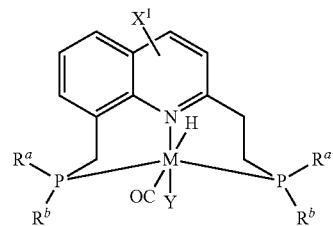

(VII)

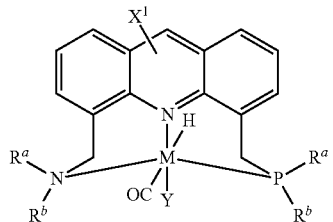

(VIII)

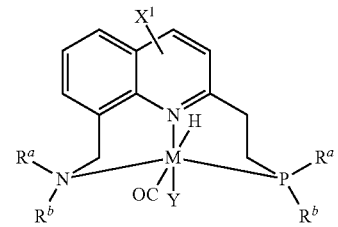

(IX)

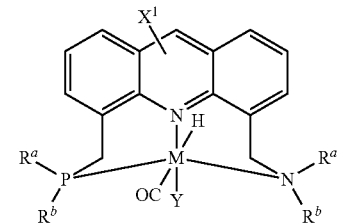

(X)

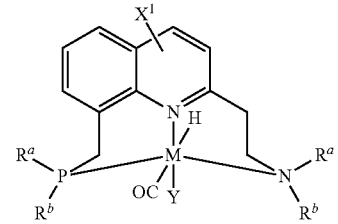

(XI)

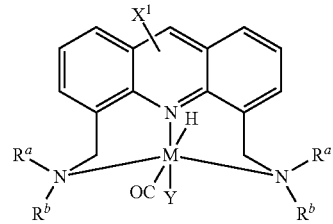

(XII)

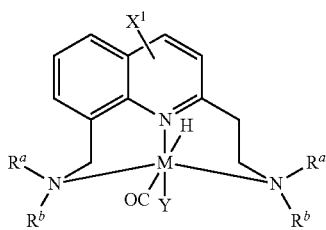

(XIII)

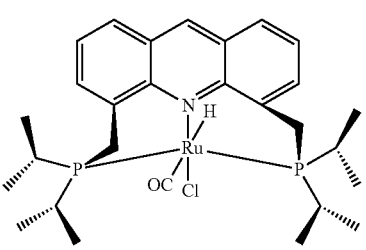

(XIVa)

In a further preferred embodiment, the process according to the invention is carried out in the presence of at least one complex catalyst from the group of catalysts of the formula (VI), (VII), (VIII), (IX), (X), (XI), (XII) and (XIII), where $R^a$ and $R^b$ independently of one another, are unsubstituted or at least mono-substituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

Y is a monoanionic ligand selected from the group H, F, Cl, Br, OCOR, $OCOCF_3$, $OSO_2R$, $OSO_2CF_3$, CN, OH, OR, $N(R)_2$;

R is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl, $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;

$X^1$ is one, two or three substituents on one or more atoms of the acridinyl unit or one or two substituents on one or more atoms of the quinolinyl unit, where $X^1$, independently of the others, is selected from the group consisting of hydrogen, F, Cl, Br, I, OH, $NH_2$, $NO_2$, —NC(O)R, $C(O)NR_2$, —OC(O)R, —C(O)OR, CN and borane derivatives which are obtainable from the catalyst of the formula (I) by reaction with $NaBH_4$, and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl and $C_5$-$C_{10}$-heteroaryl comprising at least one heteroatom selected from N, O and S;

and

M is ruthenium or iridium.

In a further preferred embodiment, the process according to the invention is carried out in the presence of at least one complex catalyst from the group of catalysts of the formula (VI), (VII), (VIII), (IX), (X), (XI), (XII) and (XIII), where $R^a$ and $R^b$ independently of one another, are methyl, ethyl, isopropyl, tert-butyl, cyclohexyl, cyclopentyl, phenyl or mesityl;

Y is a monoanionic ligand selected from the group H, F, Cl, Br, $OCOCH_3$, $OCOCF_3$, $OSO_2CF_3$, CN and OH;

$X^1$ is a substituent on an atom of the acridinyl unit or a substituent on an atom of the quinolinyl unit, where $X^1$ is selected from the group consisting of hydrogen, F, Cl, Br, OH, $NH_2$, $NO_2$, —NC(O)R, $C(O)NR_2$, —OC(O)R, —C(O)OR, CN and borane derivatives which are obtainable from the catalyst of the formula (I) by reaction with $NaBH_4$, and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{10}$-aryl and $C_5$-$C_{10}$-heteroaryl comprising at least one heteroatom selected from N, O and S;

M is ruthenium or iridium.

In a further preferred embodiment, the process according to the invention is carried out in the presence of at least one complex catalyst from the group of catalysts of the formula (VI), (VII), (VIII), (IX), (X), (XI), (XII) and (XIII), where $R^a$ and $R^b$, independently of one another, are methyl, ethyl, isopropyl, tert-butyl, cyclohexyl, cyclopentyl, phenyl or mesityl;

Y is monoanionic ligand from the group F, Cl, Br, I, $OCOCH_3$, $OCOCF_3$, $OSO_2CF_3$, CN and OH;

$X^1$ is hydrogen;

and

M is ruthenium or iridium.

In a particularly preferred embodiment, $L^3$ is carbon monoxide (CO).

In a particularly preferred embodiment, the process according to the invention is carried out in the presence of a complex catalyst of the formula (XIVa):

In a very particularly preferred embodiment, the process according to the invention is carried out in the presence of a complex catalyst of the formula (XIVb):

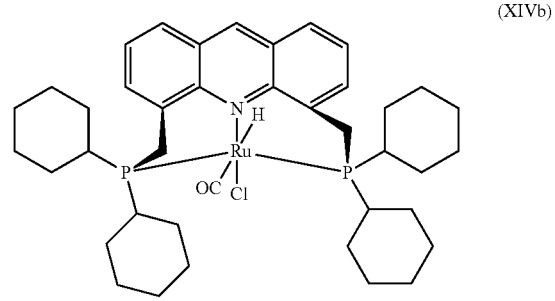

(XIVb)

In a further particularly preferred embodiment, the process according to the invention is carried out in the presence of at least one homogeneously dissolved complex catalyst of the formula (XV) in which $R^1$, $R^2$, $R^3$, $L^1$, $L^2$ and $L^3$ have the meanings described above.

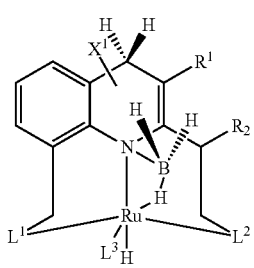

(XV)

Complex catalysts of the formula (XV) are obtainable by reacting catalysts of the formula (I) with sodium borohydride (NaBH$_4$). The reaction follows the general reaction equation:

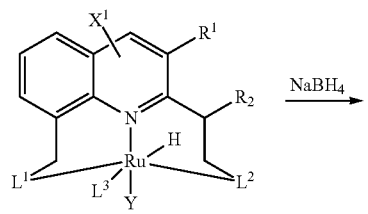

In a further particularly preferred embodiment, the process according to the invention is carried out in the presence of a complex catalyst of the formula (XVIa):

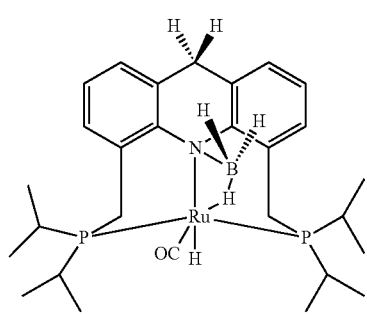

(XVIa)

In a further particularly preferred embodiment, the process according to the invention is carried out in the presence of a complex catalyst of the formula (XVIb):

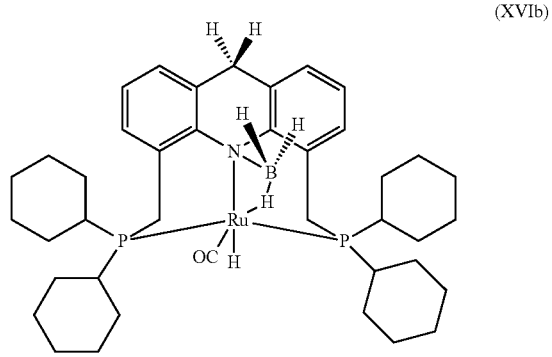

(XVIb)

The borane derivative of the formula (XVIa) is accessible according to the following reaction equation:

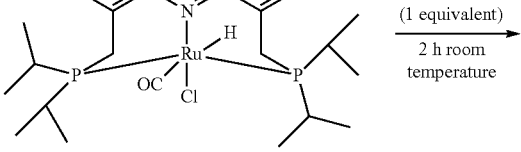

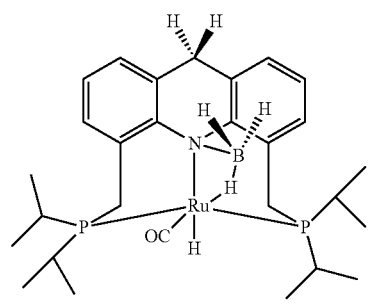

The borane derivative of the formula (XVIb) is accessible according to the following reaction equation:

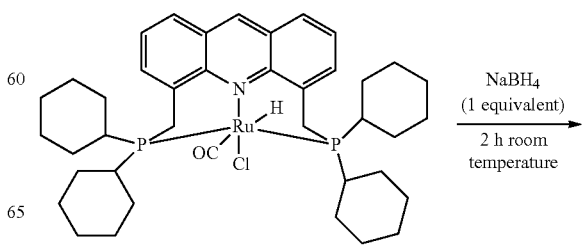

-continued

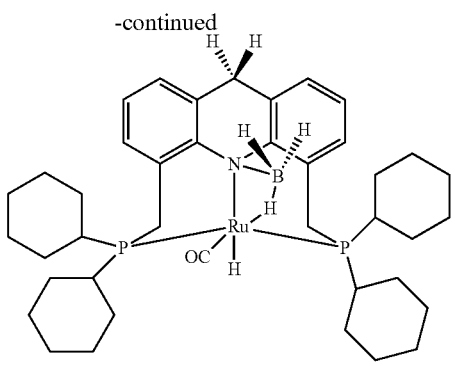

Within the context of the present invention, $C_1$-$C_{10}$-alkyl are understood as meaning branched, unbranched, saturated and unsaturated groups. Preference is given to alkyl groups having 1 to 6 carbon atoms ($C_1$-$C_6$-alkyl). More preference is given to alkyl groups having 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

In the present case, $C_3$-$C_{10}$-cycloalkyl is understood as meaning saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted with one or more substituents, as has been defined above in relation to the group $C_1$-$C_{10}$-alkyl.

Within the context of the present invention, $C_5$-$C_{10}$-aryl is understood as meaning an aromatic ring system having 5 to 10 carbon atoms. The aromatic ring system can be monocyclic or bicyclic. Examples of aryl groups are phenyl, naphthyl such as 1-naphthyl or 2-naphthyl. The aryl group can be unsubstituted or substituted with one or more substituents as defined above under $C_1$-$C_{10}$-alkyl.

Within the context of the present invention, $C_5$-$C_{10}$-heteroaryl is understood as meaning a heteroaromatic system which comprises at least one heteroatom selected from the group N, O and S. The heteroaryl groups can be monocyclic or bicyclic. For the case that nitrogen is a ring atom, the present invention also comprises N-oxides of the nitrogen-comprising heteroaryls. Examples of heteroaryls are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted with one or more substituents which have been defined above under $C_1$-$C_{10}$-alkyl.

Within the context of the present invention, $C_3$-$C_{10}$-heterocyclyl is understood as meaning five- to ten-membered ring systems which comprise at least one heteroatom from the group N, O and S. The ring systems can be monocyclic or bicyclic. Examples of suitable heterocyclic ring systems are piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl and tetrahydropyranyl.

In a further embodiment, the process according to the invention uses at least one complex catalyst which comprises at least one element selected from the groups 8, 9 and 10 of the Periodic Table of the Elements (nomenclature according to IUPAC), and also at least one phosphorus donor ligand of the general formula (XXI),

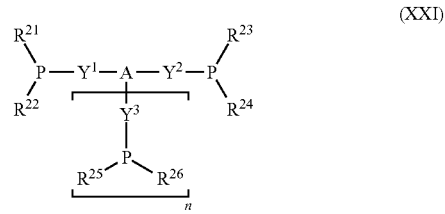

(XXI)

where
n is 0 or 1;
$R^{21}$, $R^{22}$, $R^{23}$, $R^{24}$, $R^{25}$, $R^{26}$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S, where the substituents are selected from the group consisting of: F, Cl, Br, OH, CN, $NH_2$ and $C_1$-$C_{10}$-alkyl;
A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
where the substituents are selected from the group consisting of: $C_1$-$C_4$-alkyl, phenyl, F, Cl, Br, OH, $OR^{27}$, $NH_2$, $NHR^{27}$ or $N(R^{27})_2$,
where $R^{27}$ is selected from $C_1$-$C_{10}$-alkyl and $C_5$-$C_{10}$-aryl;
or
ii) a bridging group of the formula (XXII) or (XXIII):

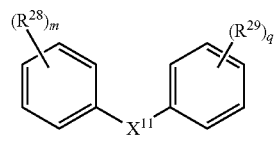

(XXII)

(XXIII)

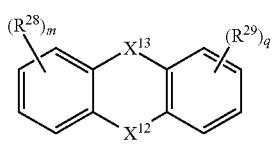

m, q are, independently of one another, 0, 1, 2, 3 or 4;
$R^{28}$, $R^{29}$ are, independently of one another, selected from the group $C_1$-$C_{10}$-alkyl, F, Cl, Br, OH, $OR^{27}$, $NH_2$, $NHR^{27}$ and $N(R^{27})_2$,
where $R^{27}$ is selected from $C_1$-$C_{10}$-alkyl and $C_5$-$C_{10}$-aryl;
$X^{11}$, $X^{12}$ are, independently of one another, NH, O or S;
$X^{13}$ is a bond, NH, $NR^{30}$, O, S or $CR^{31}R^{32}$;
$R^{30}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$R^{31}$, $R^{32}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$Y^1$, $Y^2$, $Y^3$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^{27}$, CN, $NH_2$, $NHR^{27}$, $N(R^{27})_2$ and $C_1$-$C_{10}$-alkyl,
where $R^{27}$ is selected from $C_1$-$C_{10}$-alkyl and $C_5$-$C_{10}$-aryl.

According to the invention, A is a bridging group. For the case that A is selected from the group unsubstituted or at least monosubstituted $C_1$-$C_6$-alkane, $C_3$-$C_{10}$-cycloalkane, $C_3$-$C_{10}$-heterocycloalkane, $C_5$-$C_{14}$-aromatic and $C_5$-$C_6$-heteroaromatic and bridging groups of the formula (II) or (III), for the case (n=0), two hydrogen atoms of the bridging group are replaced by bonds to the adjacent substituents $Y^1$ and $Y^2$. For the case (n=1), three hydrogen atoms of the bridging group are replaced by three bonds to the adjacent substituents $Y^1$, $Y^2$ and $Y^3$.

For the case that A is P (phosphorus), the phosphorus forms for the case (n=0) two bonds to the adjacent substituents $Y^1$ and $Y^2$ and one bond to a substituent selected from the group consisting of $C_1$-$C_4$-alkyl and phenyl. For the case (n=1), the phosphorus forms three bonds to the adjacent substituents $Y^1$, $Y^2$ and $Y^3$.

For the case that A is N (nitrogen), the nitrogen for the case (n=0) forms two bonds to the adjacent substituents $Y^1$ and $Y^2$ and one bond to a substituent selected from the group consisting of $C_1$-$C_4$-alkyl and phenyl. For the case (n=1), the nitrogen forms three bonds to the adjacent substituents $Y^1$, $Y^2$ and $Y^3$.

For the case that A is O (oxygen), n=0. The oxygen forms two bonds to the adjacent substituents $Y^1$ and $Y^2$.

Preference is given to complex catalysts which comprise at least one element selected from ruthenium and iridium.

In a preferred embodiment, the process according to the invention is carried out in the presence of at least one complex catalyst which comprises at least one element selected from the groups 8, 9 and 10 of the Periodic Table of the Elements and also at least one phosphorus donor ligand of the general formula (XXI), where
n is 0 or 1;
$R^{21}$, $R^{22}$, $R^{23}$, $R^{24}$, $R^{25}$, $R^{26}$ are, independently of one another, unsubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S;
A is
i) a bridging group selected from the group unsubstituted $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S;
or
ii) a bridging group of the formula (XXII) or (XXIII):

(XXII)

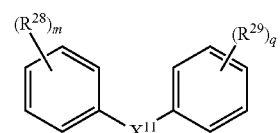

(XXIII)

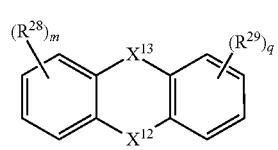

m, q are, independently of one another, 0, 1, 2, 3 or 4;
$R^{28}$, $R^{29}$ are, independently of one another, selected from the group $C_1$-$C_{10}$-alkyl, F, Cl, Br, OH, $OR^{27}$, $NH_2$, $NHR^{27}$ and $N(R^{27})_2$,
where $R^{27}$ is selected from $C_1$-$C_{10}$-alkyl and $C_5$-$C_{10}$-aryl;
$X^{11}$, $X^{12}$ are, independently of one another, NH, O or S;
$X^{13}$ is a bond, NH, $NR^{30}$, O, S or $CR^{31}R^{32}$;
$R^{30}$ is unsubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S;
$R^{31}$, $R^{32}$ are, independently of one another, unsubstituted $C_1$-$C_{10}$-alkyl, $C_1$-$C_{10}$-alkoxy, C3-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S;
$Y^1$, $Y^2$, $Y^3$ are, independently of one another, a bond, unsubstituted methylene, ethylene, trimethylene, tetramethylene, pentamethylene or hexamethylene.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (XXV),

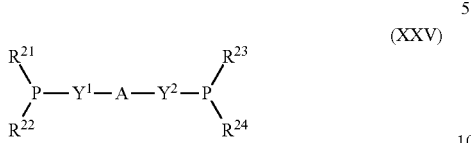
(XXV)

where
$R^{21}$, $R^{22}$, $R^{23}$, $R^{24}$ are, independently of one another, unsubstituted or at least monosubstituted $C_1$-$C_{10}$-alkyl, $C_1$-$C_4$-alkyldiphenylphosphine (—$C_1$-$C_4$-alkyl-P(phenyl)$_2$), $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
A is
i) a bridging group selected from the group unsubstituted or at least monosubstituted N, O, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
where the substituents are selected from the group consisting of: $C_1$-$C_4$-alkyl, phenyl, F, Cl, Br, OH, $OR^{27}$, $NH_2$, $NHR^{27}$ or $N(R^{27})_2$,
where $R^{27}$ is selected from $C_1$-$C_{10}$-alkyl and $C_5$-$C_{10}$-aryl;
or
ii) a bridging group of the formula (XXII) or (XXIII):

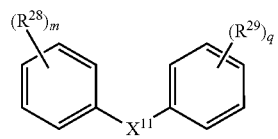
(XXII)

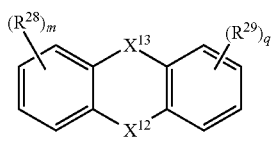
(XXIII)

m, q are, independently of one another, 0, 1, 2, 3 or 4;
$R^{28}$, $R^{29}$ are, independently of one another, selected from the group $C_1$-$C_{10}$-alkyl, F, Cl, Br, OH, $OR^{27}$, $NH_2$, $NHR^{27}$ and $N(R^{27})_2$,
where $R^{27}$ is selected from $C_1$-$C_{10}$-alkyl and $C_5$-$C_{10}$-aryl;
$X^{11}$, $X^{12}$ are, independently of one another, NH, O or S, $X^{13}$ is a bond, NH, $NR^{30}$, O, S or $CR^{31}R^{32}$;
$R^{30}$ is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$R^{31}$, $R^{32}$ are, independently of one another, unsubstituted or at least monosubstituted $C_1$-$C_{10}$-alkyl, $C_1$-$C_{10}$-alkoxy, $C_3$-$C_{10}$-cycloalkyl, $C_3$-$C_{10}$-cycloalkoxy, $C_3$-$C_{10}$-heterocyclyl comprising at least one heteroatom selected from N, O and S, $C_5$-$C_{14}$-aryl, $C_5$-$C_{14}$-aryloxy or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
$Y^1$, $Y^2$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^{27}$, CN, $NH_2$, $NHR^{27}$, $N(R^{27})_2$ and $C_1$-$C_{10}$-alkyl,
where $R^{27}$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (XXVI),

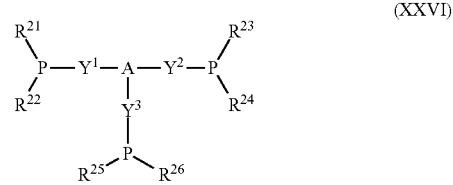
(XXVI)

where
$R^{21}$, $R^{22}$, $R^{23}$, $R^{24}$, $R^{25}$, $R^{26}$ are, independently of one another, unsubstituted or at least monosubstituted $C_1$-$C_{10}$-alkyl, $C_1$-$C_4$-alkyldiphenylphosphine, $C_3$-$C_{10}$-cycloalkyl, $C_3$-$C_{10}$-heterocyclyl comprising at least one heteroatom selected from N, O and S, $C_5$-$C_{14}$-aryl or $C_5$-$C_{10}$-heteroaryl comprising at least one heteroatom selected from N, O and S,
where the substituents are selected from the group consisting of: F, Cl, Br, OH, CN, $NH_2$ and $C_1$-$C_{10}$-alkyl;
A is a bridging group selected from the group unsubstituted or at least mono-substituted N, P, $C_1$-$C_6$-alkane, $C_3$-$C_{10}$-cycloalkane, $C_3$-$C_{10}$-heterocycloalkane comprising at least one heteroatom selected from N, O and S, $C_5$-$C_{14}$-aromatic and $C_5$-$C_6$-heteroaromatic comprising at least one heteroatom selected from N, O and S,
where the substituents are selected from the group consisting of: $C_1$-$C_4$-alkyl, phenyl, F, Cl, Br, OH, $OR^{27}$, $NH_2$, $NHR^{27}$ or $N(R^{27})_2$,
where $R^{27}$ is selected from $C_1$-$C_{10}$-alkyl and $C_5$-$C_{10}$-aryl;
$Y^1$, $Y^2$, $Y^3$ are, independently of one another, a bond, unsubstituted or at least monosubstituted methylene, ethylene, trimethylene, tetramethylene, pentamethylene or hexamethylene,
where the substituents are selected from the group consisting of: F, Cl, Br, OH, $OR^{27}$, CN, $NH_2$, $NHR^{27}$, $N(R^{27})_2$ and $C_1$-$C_{10}$-alkyl,
where $R^{27}$ is selected from $C_1$-$C_{10}$-alkyl and $C_5$-$C_{10}$-aryl.

In a further preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (XXV), where $R^{21}$, $R^{22}$, $R^{23}$, $R^{24}$ are, independently of one another, methyl, ethyl, isopropyl, tert-butyl, cyclopentyl, cyclohexyl, phenyl, or mesityl;

A is
i) a bridging group selected from the group methane, ethane, propane, butane, cyclohexane, benzene, napthalene and anthracene;
or
ii) a bridging group of the formula (XXVII) or (XXVII):

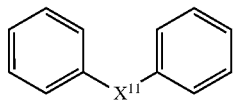

(XXVII)

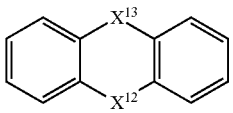

(XXVIII)

$X^{11}$, $X^{12}$ are, independently of one another, NH, O or S;
$X^{13}$ is a bond, NH, O, S or $CR^{31}R^{32}$;
$R^{31}$, $R^{32}$ are, independently of one another, unsubstituted $C_1$-$C_{10}$-alkyl;
$Y^1$, $Y^2$ are, independently of one another, a bond, methylene or ethylene.

In a particularly preferred embodiment, the process according to the invention is carried out in the presence of at least one complex catalyst which comprises at least one element selected from groups 8, 9 and 10 of the Periodic Table of the Elements and also at least one phosphorus donor ligand of the general formula (XXIX) or (XXX),

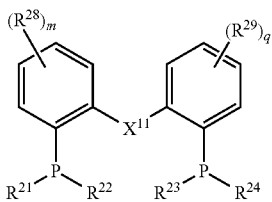

(XXIX)

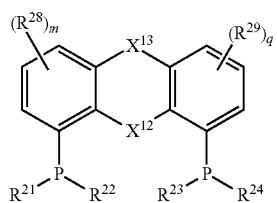

(XXX)

where for m, q, $R^{21}$, $R^{22}$, $R^{23}$, $R^{24}$, $R^{28}$, $R^{29}$, $X^{19}$, $X^{12}$ and $X^{13}$, the definitions and preferences listed above are applicable.

In a further particularly preferred embodiment, the process according to the invention is carried out in the presence of at least one complex catalyst which comprises at least one element selected from the group ruthenium and iridium and also at least one phosphorus donor ligand selected from the group 1,2-bis(diphenylphosphino)ethane (dppe), 1,3-bis(diphenylphosphino)propane (dppp), 1,4-bis(diphenylphosphino) butane (dppb), 2,3-bis(dicyclohexylphosphino)ethane (dcpe), 4,5-bis(diphenylphosphino)-9,9-dimethylxanthene (xantphos), bis(2-diphenylphosphinoethyl)phenylphosphine and 1,1,1-tris(diphenylphosphinomethyl)ethane (triphos).

In a further particularly preferred embodiment, the process according to the invention is carried out in the presence of a complex catalyst which comprises ruthenium and at least one phosphorus donor ligand selected from the group 4,5-bis (diphenylphosphino)-9,9-dimethylxanthene (xantphos), bis (2-diphenylphosphino-ethyl)phenylphosphine and 1,1,1-tris (diphenylphosphinomethyl)ethane (triphos).

In a further particularly preferred embodiment, the process according to the invention is carried out in the presence of a complex catalyst which comprises iridium and also at least one phosphorus donor ligand selected from the group 4,5-bis (diphenylphosphino)-9,9-dimethylxanthene (xantphos), bis (2-diphenylphosphino-ethyl)phenylphosphine and 1,1,1-tris (diphenylphosphinomethyl)ethane (triphos).

Within the context of the present invention, $C_1$-$C_{10}$-alkyl is understood as meaning branched, unbranched, saturated and unsaturated groups. Preference is given to alkyl groups having 1 to 6 carbon atoms ($C_1$-$C_6$-alkyl). More preference is given to alkyl groups having 1 to 4 carbon atoms ($C_1$-$C_4$-alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted with one or more substituents selected from the group F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from N, O, S, oxo, $C_3$-$C_{10}$-cycloalkyl, phenyl, $C_5$-$C_{10}$-heteroaryl comprising at least one heteroatom selected from N, O, S, $C_5$-$C_{10}$-heterocyclyl comprising at least one heteroatom selected from N, O, S, naphthyl, amino, $C_1$-$C_{10}$-alkylamino, $C_5$-$C_{10}$-arylamino, $C_5$-$C_{10}$-heteroarylamino comprising at least one heteroatom selected from N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$-carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol or $C_1$-$C_{10}$-alkylsulfonyl.

The above definition for $C_1$-$C_{10}$-alkyl applies correspondingly to $C_1$-$C_{30}$-alkyl and to $C_1$-$C_6$-alkane.

$C_3$-$C_{10}$-cycloalkyl is understood in the present case as meaning saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted with one or more substituents as has been defined above in connection with the group $C_1$-$C_{10}$-alkyl.

The definition of $C_3$-$C_{10}$-cycloalkyl specified above applies accordingly to $C_3$-$C_{10}$-cycloalkane.

The homogeneous catalysts can be generated directly in their active form or else are only generated under the reaction conditions starting from customary precursors with the addition of the corresponding ligands. Customary precursors are, for example, [Ru(p-cymene)$Cl_2$]$_2$, [Ru(benzene)$Cl_2$]$_n$, [Ru (CO)$_2Cl_2$]$_n$, [Ru(CO)$_3Cl_2$]$_2$ [Ru(COD)(allyl)], [$RuCl_3*H_2O$], [Ru(acetylacetonate)$_3$], [Ru(DMSO)$_4Cl_2$], [Ru($PPh_3$)$_3$(CO)(H)Cl], [Ru($PPh_3$)$_3$(CO)$C_2$], [Ru($PPh_3$)$_3$ (CO)(H)$_2$], [Ru($PPh_3$)$_3Cl_2$], [Ru(cyclopenta-dienyl)($PPh_3$)$_2$ Cl], [Ru(cyclopentadienyl)(CO)$_2$Cl], [Ru(cyclopentadienyl)(CO)$_2$H], [Ru(cyclopentadienyl)(CO)$_2$]$_2$, [Ru(pentamethylcyclopentadienyl)(CO)$_2$Cl], [Ru(pentamethylcylopentadienyl)(CO)$_2$H], [Ru(pentamethylcyclopentadienyl)(CO)$_2$]$_2$, [Ru(indenyl)(CO)$_2$Cl], [Ru(indenyl)(CO)$_2$H], [Ru(indenyl)(CO)$_2$]$_2$, Ruthenocene, [Ru(binap)C$_2$], [Ru(bipyridine)$_2$Cl$_2$*2H$_2$O], [Ru(COD)Cl$_2$]$_2$, [Ru(pentamethylcyclopentadienyl)(COD)Cl], [Ru$_3$(CO)$_{12}$], [Ru(tetraphenylhydroxycyclopentadienyl)(CO)$_2$H], [Ru(PMe$_3$)$_4$(H)$_2$], [Ru(PEt$_3$)$_4$(H)$_2$], [Ru(PnPr$_3$)$_4$(H)$_2$], [Ru(PnBu$_3$)$_4$(H)$_2$], [Ru(PnOctyl$_3$)$_4$(H)$_2$], [IrCl$_3$*H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(cyclopentadienyl)Cl$_2$]$_2$, [Ir(pentamethylcyclopentadenyl)C$_2$]$_2$, [Ir(cylopentadienyl)(CO)$_2$], [Ir(pentamethylcyclopentadienyl)(CO)$_2$], [Ir(PPh$_3$)$_2$(CO)(H)], [Ir(PPh$_3$)$_2$(CO)(Cl)], [Ir(PPh$_3$)$_3$(Cl)].

Alcohol Amination (Step (a))

The alcohol amination in step (a) takes place by homogeneously catalyzed reaction of one or more hydroxyl-group-comprising starting materials with ammonia in the presence of at least one of the complex catalysts described above.

During the amination reaction, according to the invention, at least one hydroxyl group (—OH) of the starting material is reacted with ammonia to give a primary amino group (—NH$_2$), with the formation of in each case 1 mol of water of reaction per mole of reacted hydroxyl group.

Thus, in the case of the reaction of alkanolamines which have only one hydroxyl group, the corresponding diamines are formed. The reaction of monoaminoethanol thus leads to the corresponding 1,2-diaminoethane.

In the case of the reaction of starting materials which have a further hydroxyl group (diols), reaction with ammonia leads to the corresponding primary diamines or alkanol-amines depending on the reaction conditions. The reaction of 1,2-ethylene glycol thus leads to the corresponding 1,2-diaminoethane or monoaminoethanol.

In the case of the reaction of starting materials which have two further hydroxyl groups as well as one hydroxyl group (triols), two or three hydroxyl groups are reacted with ammonia to give the corresponding primary diamines or triamines. The formation of diamines or triamines can be controlled here via the amount of ammonia used and via the reaction conditions. The reaction of glycerol thus leads to the corresponding 1,3-diaminopropanol (1,3-diaminopropan-2-ol) or to 1,2,3-triaminopropane.

In the case of the reaction of starting material which, as well as the one hydroxyl group, have more than three further hydroxyl groups (polyols), two, three or more hydroxyl groups are reacted with ammonia to give the corresponding primary diamines, triamines or polyamines. The formation of the corresponding primary diamines, triamines or polyamines can be controlled here via the amount of ammonia used and via the reaction conditions.

Within the context of the present invention, homogeneously catalyzed is understood as meaning that the catalytically active part of the complex catalyst is present in at least partially dissolved form in the liquid reaction medium. In a preferred embodiment, at least 90% of the complex catalyst used in the process is present in dissolved form in the liquid reaction medium, more preferably at least 95%, especially preferably more than 99%, most preferably the complex catalyst is present in completely dissolved form in the liquid reaction medium (100%), in each case based on the total amount in the liquid reaction medium.

The amount of metal component in the catalyst, preferably ruthenium or iridium, is generally 0.1 to 5000 ppm by weight, in each case based on the total liquid reaction mixture in the reaction space.

The reaction in step (a) takes place in the liquid phase generally at a temperature of from 20 to 250° C. Preferably, the process according to the invention is carried out at temperatures in the range from 100° C. to 200° C., particularly preferably in the range from 110 to 160° C.

The reaction is generally carried out at a total pressure of from 0.1 to 20 MPa absolute, which can either be the intrinsic pressure of the solvent and of the ammonia at the reaction temperature, and also the pressure of a gas such as nitrogen, argon or hydrogen. Preferably, the process according to the invention is carried out at a total pressure up to 15 MPa absolute, particularly preferably at a total pressure of up to MPa absolute.

The aminating agent (ammonia) can be used in stoichiometric, substoichiometric or superstoichiometric amounts with regard to the hydroxyl groups to be aminated. In a preferred embodiment, ammonia is used in a 1.0- to 250-fold, preferably in a 1.5- to 100-fold, especially in a 2- to 10-fold, molar excess per mole of hydroxyl groups to be reacted in the starting material. Even higher excesses of ammonia are possible. The ammonia can be added in gaseous form, in liquid form or dissolved in one of the solvents.

According to the invention, the reaction takes place in the presence of at least one nonpolar solvent. In this connection, one nonpolar solvent or mixtures of two or more nonpolar solvents can be used.

The nonpolar solvent is generally selected from saturated hydrocarbons such as hexane, heptane, octane and cyclohexane; linear and cyclic ethers such as diethyl ether, 1,4-dioxane, tert-butyl methyl ether, tert-amylalcohol, tert-butanol, diglyme and 1,2-dimethoxyethane and aromatic hydrocarbons such as benzene, toluene, o-, m-, p-xylene and mesitylene and mixtures thereof. Preference is given to using aromatic solvents, particularly preferably toluene, o-, m-, p-xylene, mesitylene and mixtures thereof.

In this connection, nonpolar solvent and homogeneous catalyst are selected such that the catalyst accumulates in the nonpolar phase (B) obtained following the phase separation in step (b). According to the invention, accumulated is understood as meaning that the quantitative partition coefficient $P_{MC}$=[amount of dissolved catalyst in the nonpolar phase (B)]/[amount of dissolved catalyst in the polar product phase (A)] is greater than 1. Preferably, $P_{Mc}$ is at least 1.5, particularly preferably at least 5.

In a preferred embodiment, nonpolar solvent and homogeneous catalyst are selected such that the catalyst dissolves better in the nonpolar phase (B) obtained following the phase separation in step (b) than in the polar phase (A). The catalyst concentration is then higher in the nonpolar phase (B) than in the polar phase (A), i.e. the partition coefficient $P_{C1}$=[concentration of the dissolved catalyst in the nonpolar phase (B)]/[concentration of the dissolved catalyst in the polar product phase (A)] is greater than 1. Preferably, $P_C$ is at least 1.5, particularly preferably at least 5.

The choice of the homogeneous catalyst and of the nonpolar solvent is usually made by means of a simple experiment in which the partition coefficient P of the chosen catalyst is determined experimentally under the planned process conditions together with the substrate and product and also the polar solvent. In particular, the lipophilicity of the catalyst and thus its solubility in nonpolar and/or polar phases can be influenced in a targeted manner by the choice of ligands.

As a rule, the nonpolar solvent is selected such that the homogeneous catalyst preferentially dissolves therein compared to the polar solvent. According to the invention, this means that the partition coefficient $P_{C2}$=[concentration of the catalyst in the nonpolar solvent]/[concentration of the catalyst in the polar solvent] is greater than 1, preferably at least 2 and particularly preferably at least 5. Further preferred $P_{C2}$ is at least 1.5.

For the reaction in the liquid phase, ammonia, the at least one alcohol, the at least one nonpolar solvent are usually fed into a reaction space together with the complex catalyst. The reaction can be carried out in customary devices or reactors known to the person skilled in the art for liquid-gas reactions in which the catalyst is present in homogeneously dissolved form in the liquid phase. For the process according to the invention, all reactors can in principle be used which are fundamentally suitable for gas/liquid reactions under the stated temperature and the stated pressure. Suitable standard reactors for gas-liquid and for liquid-liquid reaction systems are discussed for example in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, Chapter 3.3 "Reactors for gas-liquid reactions". Examples which may be mentioned are stirred-tank reactors, tubular reactors or bubble column reactors. The introduction of ammonia, starting material, nonpolar solvent and complex catalyst can take place here simultaneously or separately from one another. The reaction can be carried out here discontinuously in a batch procedure or continuously, semicontinuously with or without recycling. The average residence time in the reaction space is generally 15 minutes to 100 hours.

The product mixture (P) obtained in step (a) comprises the homogeneous catalyst, the amination product, nonpolar solvent, unreacted starting materials and any by-products formed, and also water formed during the amination. It may also be advantageous to continuously remove the water formed during the reaction from the reaction mixture. The water of reaction can be separated off directly by distillation from the reaction mixture or as azeotrope with the addition of a suitable solvent (entrainer) and using a water separator, or can be removed by adding water-removing auxiliaries.

In step (b) of the process according to the invention, a phase separation of the product mixture (P) obtained in step (a) takes place, optionally after lowering the temperature and/or adding at least one polar solvent which has a miscibility gap with the nonpolar solvent used in step (a), to give at least one polar product phase (A) and at least one nonpolar phase (B) comprising at least some of the catalyst used, and separating off the nonpolar phase (B).

Both phases (A) and (B) are liquid phases, the catalyst being present in accumulated form in the nonpolar phase (B), and the amination product being present in accumulated form in the polar phase. With regard to the amination product, "accumulated" in the present case means that the quantitative partition coefficient of the amination product $P_A$=[amount of amination product in the polar phase (A)]/[amount of amination product in the nonpolar phase (B)] is greater than 1, preferably at least 1.5, particularly preferably at least 5.

In a preferred embodiment, the polar solvent is selected such that the amination product dissolves better in the polar phase (A) obtained following phase separation in step (b) than in the nonpolar phase (B). The amination product concentration is then higher in the polar phase (A) than in the nonpolar phase (B), i.e. the partition coefficient of the amination product $P_{A1}$=[concentration of the amination product in the polar phase (A)]/[concentration of the amination product in the nonpolar phase (B)] is greater than 1, preferably at least 1.5, particularly preferably at least 5.

Depending on the choice of components, it is possible that the product mixtures (P) is present in single-phase liquid form after step (a). In this case, a phase separation can be achieved by cooling and/or adding one or more polar solvents.

Suitable polar solvents are, for example, water, dimethylformamide, formamide, acetonitrile, the alcohol(s)/alkanolamine(s) used as starting materials in step (a), and mixtures thereof. In addition, the product can also be used as solvent. Preference is given to using water. The polar solvent can be added either already to the reaction mixture before or in step (a), or after the reaction in step (b) in addition to the water of reaction that is formed during the reaction.

According to the invention, the polar solvent should be matched to the nonpolar solvent and the amination product that is formed in such a way that the amination product is present in accumulated form in the polar phase (A). The selection of nonpolar and polar solvent generally takes place by simple experimentation, in which the solubility of the desired product is determined experimentally in the two phases (A) and (B) under the planned process conditions.

As a rule, the polar solvent is selected such that the amination product preferentially dissolves therein compared to the nonpolar solvent used. According to the invention, this means that the partition coefficient $P_{A2}$=[concentration of amination product in polar solvent]/[concentration of amination product in nonpolar solvent] is greater than 1, preferably at least 2 and particularly preferably at least 5. Further preferred $P_{A2}$ is at least 1.5.

Within the context of the present invention, in each case it is possible to use one solvent or mixtures of 2 or more solvents. This applies to the nonpolar solvents and also the polar solvents.

The dielectric constant DC can be used as a measure for assigning a solvent to the group polar/nonpolar. Solvents with DC greater than about 15 are usually regarded as polar (e.g. acetonitrile has a DC of about 37), solvents with a lower DC are usually regarded as nonpolar, for example the DC of benzene is 2.28.

Even if the product mixture obtained in step (a) is already present in two phases, the addition of polar solvent may be advantageous if, as a result, a more favorable partition of the catalyst and of the amination product in the two phases (A) and (B) is achieved. The same applies to the lowering of the temperature.

The phase separation of the two phases (A) and (B) in step (b) generally takes place by gravimetric phase separation. The reaction space in which the reaction according to step (a) has taken place, for example a reactor, can serve as phase separation vessel. The separation of two liquid phases is per se a standard procedure which is known to the person skilled in the art. Standard methods and processes are described, for example, in E. Müller et al., "Liquid-Liquid Extraction" in Ullmann's Encyclopedia of Industrial Chemistry, 2005, Wiky-VCH-Verlag, 10.1002/14356007.603-06, Chapter 3, "Apparatus".

In step (c) of the process according to the invention, at least some of the phase (B) separated off in step (b), is returned again to the reaction in step (a), optionally after one or more steps for the purposes of purification, such as distillation. In this connection, the entire separated-off nonpolar phase (B) can be returned, although it may also be sensible, for the purposes of removing undesired by-products and impurities, to remove some of the nonpolar phase from the process in order to avoid an accumulation of undesired components in the process.

As a rule, the polar phase will also comprise at least small amounts of the catalyst. If it is necessary to further reduce the catalyst fraction in the polar phase (A), then it can be extracted with a nonpolar solvent. The extraction of the catalyst can be carried out in any suitable device known to the person skilled in the art, preferably in countercurrent extraction columns, mixer settler cascades or combinations of mixer settler apparatuses with extraction columns. The nonpolar extract comprising the catalyst can then, optionally after removing excess nonpolar solvent by evaporation, be returned again to the amination reaction in step (a). Preferably, the extractant used is the nonpolar solvent used in step (a). The extraction of the catalyst from the polar product phase (B) can be carried out before or after separating off the amination product in step (d). According to a preferred embodiment, the extracted catalyst is returned at least in part to the reaction.

In step (d) of the process according to the invention, the amination product is separated off from the polar product phase (A). Thus, in step (d), the polar solvent can be separated off from the amination product by distillation and either be returned to the process or be discarded. Unreacted starting material (alcohol), any excess ammonia present or by-products can likewise be removed from the amination product by distillation. Thermal removal of the polar solvent takes place by prior art methods known to the person skilled in the art, preferably in an evaporator or in a distillation unit, comprising evaporator and column(s), which usually has a plurality of trays, arranged packing or dumped packing.

The addition of bases can have a positive effect on the product formation. Suitable bases which may be mentioned here are alkali metal hydroxides, alkaline earth metal hydroxides, alkali metal alcoholates, alkaline earth metal alcoholates, alkali metal carbonates and alkaline earth metal carbonates, which can be used in an amount of from 0.01 to 100 molar equivalents based on the metal catalyst used.

The invention is illustrated by the examples below without limiting it thereto.

EXAMPLES

General Procedure for the Catalytic Amination According to the Invention of Alcohols with Ammonia Ligand L, metal salt M or catalyst complex XIVb (for preparation see below, weighing in under inert atmosphere), solvent (sufficient for the total solvent volume to be 50 ml) and the alcohol to be reacted were introduced as initial charge under an Ar atmosphere in a 160 ml Parr autoclave (stainless steel V4A) with magnetically coupled slanted-blade stirrer (stirring speed: 200-500 revolutions/minute). The stated amount of ammonia was either precondensed at room temperature or directly metered in from the $NH_3$ pressurized-gas bottle. If hydrogen was used, this was carried out by means of iterative differential pressure metering. The steel autoclave was heated electrically up to the stated temperature and heated (internal temperature measurement) for the stated time with stirring (500 revolutions/minute). After cooling to room temperature, decompressing the autoclave and outgassing the ammonia at atmospheric pressure, 5 or 50 ml of water were added, whereupon two liquid phases were obtained, which were separated by means of phase separation. The reaction mixture was analyzed by means of GC (30 m RTX5 amine 0.32 mm 1.5 μm). The ruthenium content of the respective liquid phase was ascertained by means of atomic absorption spectroscopy. The results for the amination of 1,4-butanediol (Table 1), diethylene glycol (Table 2) and monoethylene glycol (Table 3) are given below:

Synthesis of the Catalyst Complex XIVb

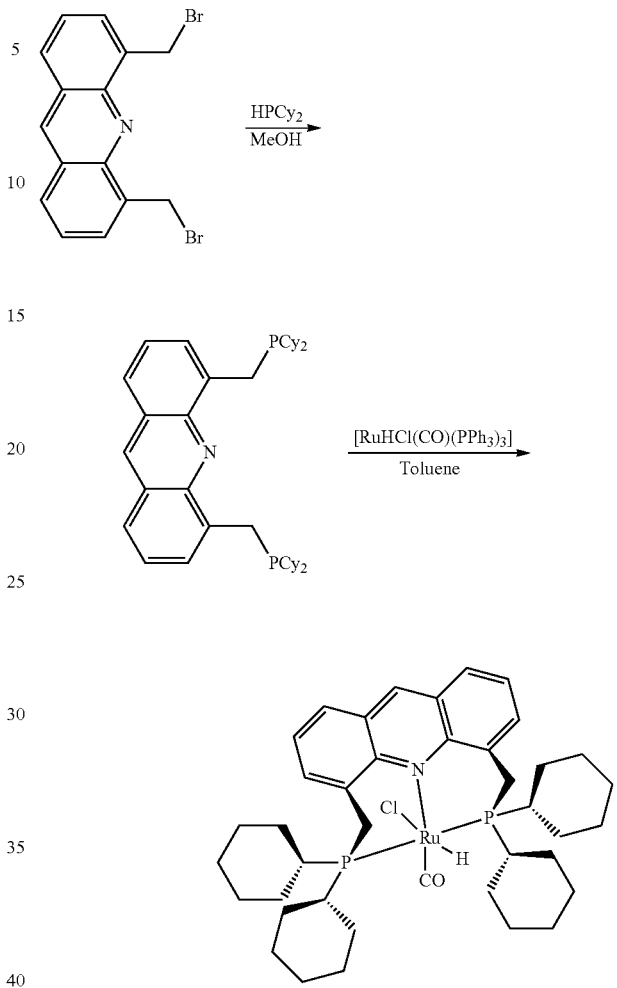

XIVb a) Synthesis of 4,5-Bis(Dicyclohexylphosphinomethyl)Acridine

A solution of 4,5-bis(bromomethyl)acridine[1] (5.2 g, 14.2 mmol) and dicyclohexylphosphine (8.18 g, 36.8 mmol) in 65 ml of anhydrous, degassed methanol was heated at 50° C. under an inert argon atmosphere for 66 h. After cooling to room temperature, triethylamine (5.72 g, 56.7 mmol) was added and the mixture was stirred for 1 h. Evaporation of the solvent produced a yellow-white solid in red oil. Extraction by means of 3×40 ml of MTBE and concentration of the filtrate produced a red-brown oil ($^1$H NMR: mixture of product & $HPCy_2$). Taking up in a small amount of warm MTBE followed by addition of ice-cooled methanol resulted in precipitation of a yellow, microcrystalline solid. Isolation and drying in vacuo gave air-sensitive 4,5-bis(dicyclo-hexylphosphinomethyl)acridine (2.74 g, 33%) as yellow powder. $^1$H NMR (360.63 MHz, toluene-d8): δ [ppm]=8.07 (s, 1H, H9), 7.91 (d, J=8.3 Hz, 2H, Ar—H), 7.42 (d, J=8.3 Hz, 2H, Ar—H), 7.21 (dd, J=8.3 Hz, J=7.2 Hz, 2H, Ar—H), 3.89 (bs, 4H, —$CH_2$—P), 1.96-1.85 (m, 8H, Cy-H), 1.77-1.54 (m, 20H, Cy-H), 1.26-1.07 (m, 16H, Cy-H). $^{31}$P{$^1$H}NMR (145.98 MHz, toluene-d8): δ [ppm]=2.49 (s, —$CH_2$—$P(Cy)_2$).

[1] J. Chiron, J. P. Galy, *Synlett*, 2003, 15, 2349-2350.

b) Synthesis of the Catalyst Complex XIVb 4,5-Bis(dicyclohexylphosphinomethyl)acridine (1855 mg, 3.1 mmol) and [RuHCl(CO)(PPh$_3$)$_3$]$^2$ (2678 mg, 2.81 mmol) were heated at 70° C. in 80 ml of degassed toluene for 2 h. The resulting dark-brown solution was evaporated to dryness, the residue was slurried in 3×20 ml of hexane and isolated by filtration. Drying in vacuo gave Ru-PNP pincer complex XIVb (1603 mg, 75%) as an orange-brown powder.
$^1$H NMR (360.63 MHz, toluene-d8): δ [ppm]=8.06 (s, 1H, H9), 7.43 (d, J=7.6 Hz, 2H, Ar—H), 7.33 (d, J=6.5 Hz, 2H, Ar—H), 7.06-7.02 (m, 2H, Ar—H), 5.02 (d, J=11.9 Hz, 2H, —CHH—PCy$_2$), 3.54 (d, J=12.2 Hz, 2H, —CHH—PCy$_2$), 2.87 (bs, 2H, —P(C$_a$H(CH$_2$)$_5$)$_2$), 2.54 (bs, 2H, —P(C$_b$H(CH$_2$)$_5$)$_2$), 2.18 (bs, 2H, Cy-H), 1.88-1.85 (m, 8H, Cy-H), 1.65 (bs, 6H, Cy-H), 1.42-1.35 (m, 14H, Cy-H), 1.17-0.82 (m, 12H, Cy-H), -16.29 (t, J=19.1 Hz, 1H, Ru—H).
$^{31}$P{$^1$H}NMR (145.98 MHz, toluene-d8): δ [ppm]=60.89 (s, —CH$_2$—P(Cy)$_2$).

$^2$ Literature procedure: *Inorganic Syntheses* 1974, 15, 48. See also: T. Joseph, S. S. Deshpande, S. B. Halligudi, A. Vinu, S. Ernst, M. Hartmann, *J. Mol. Cat. (A)* 2003, 206, 13-21.

TABLE 1

Reaction of 1,4-butanediol

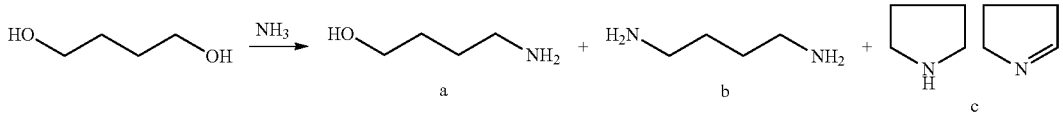

| No.[a] | T (° C.) | Time (h) | NH$_3$ [eq.][e] | Reaction pressure [bar] | Metal salt | Metal [M] (mol %)[r] | Ligand [L] | Ligand [L] (mol %)[r] | P$_{MC}$ (Ru)[q] | P$_C$ (Ru)[q] | Conversion[b] | Selectivity[c] a | b | c |
|---|---|---|---|---|---|---|---|---|---|---|---|---|---|---|
| 1[d] | 155 | 12 | 6 | 49 | [RuHCl(CO)(PPh$_3$)$_3$] | 0.1 | Triphos[f] | 0.1 | 1.8 | | 74.7 | 59.1 | 0.7 | 6.7 |
| 2[d] | 155 | 12 | 6 | 66[h] | [RuHCl(CO)(PPh$_3$)$_3$] | 0.1 | Triphos[f] | 0.1 | 3.2 | | 61.8 | 78.0 | 0.6 | 5.4 |
| 3[d] | 155 | 12 | 6 | 45 | [RuHCl(CO)(PPh$_3$)$_3$] | 0.1 | Xantphos[g] | 0.1 | 1.4 | | 35.0 | 81.8 | 0.0 | 6.4 |
| 4[d] | 155 | 60 | 6 | 61[h] | [RuHCl(CO)(PPh$_3$)$_3$] | 0.2 | Triphos[f] | 0.2 | 11.5 | 1.7 | 99.5 | 23.6 | 8.2 | 62.3 |
| 5[d] | 155 | 60 | 6 | 61[h] | [RuHCl(CO)(PPh$_3$)$_3$] | 0.1 | Triphos[f] | 0.1 | 14.0 | 2.0 | 98.5 | 34.2 | 11.4 | 49.6 |
| 6[d] | 155 | 12 | 6 | 81[i] | [RuHCl(CO)(PPh$_3$)$_3$] | 0.1 | Triphos[f] | 0.1 | 10.0 | 1.4 | 10.5 | 97.3 | 0 | 0.9 |
| 7[d] | 180 | 12 | 6 | 89[j] | [RuHCl(CO)(PPh$_3$)$_3$] | 0.1 | Triphos[f] | 0.1 | 12.0 | 1.7 | 9.2 | 97.5 | 0 | 0.8 |
| 8[k] | 155 | 12 | 6 | 90[j] | Catalyst complex XIVb | 0.1 | — | | 3.5 | 3.6 | 74.8 | 44.7 | 2.1 | 41.0 |
| 9[d] | 155 | 12 | 6 | 41 | [RuHCl(CO)(PPh$_3$)$_3$] | 0.1 | Triphos[f] | 0.1 | 2.1 | | 66.3 | 62.1 | 0.5 | 5.8 |
| 10[d] | 155 | 12 | 6 | 41 | [RuHCl(CO)(PPh$_3$)$_3$] | 0.1 | Xanthphos[g] | 0.1 | 1.6 | | 34.3 | 79.6 | 0 | 4.9 |
| 11[d] | 155 | 12 | 6 | 41 | Catalyst complex XIVb | 0.1 | | | 1.1 | | 63.0 | 71.8 | 9.3 | 17.3 |
| 12[d] | 155 | 12 | 6 | 61[h] | [RuHCl(CO)(PPh$_3$)$_3$] | 0.1 | Xanthphos[g] | 0.1 | 1.4 | | 29.3 | 79.8 | 0 | 3.3 |
| 13[d] | 155 | 12 | 6 | 61[h] | [Ru(COD)methylallyl$_2$] | 0.1 | (Tetraphos)[l] | 0.1 | 1.3 | | 10.9 | 33.2 | 0 | 0.6 |
| 14[d] | 155 | 12 | 6 | 55[h] | Catalyst complex XIVb | 0.1 | | | 1.5 | | 25 | 81 | 4.8 | 13.6 |
| 15[d] | 180 | 12 | 6 | 39[h] | [RuHCl(CO)(PPh$_3$)$_3$] | 0.2 | Triphos[f] | 0.2 | 5.7 | | 99.9 | 1.7 | 4.7 | 37.7 |
| 16[d] | 155 | 12 | 6 | 35 | [RuHCl(CO)(PPh$_3$)$_3$] | 0.2 | Triphos[f] | 0.2 | 1.8 | | 75.5 | 60.4 | 0.7 | 20.5 |
| 17[d] | 155 | 12 | 6 | 40 | Catalyst complex XIVa | 0.1 | | | 1.2 | | 56.1 | 79.7 | 3 | 16.3 |
| 18[d] | 180 | 2 | 6 | 53 | Catalyst complex XIVb | 0.2 | | | 1.1 | | 91.5 | 36.4 | 25.8 | 35.4 |
| 19[d] | 180 | 12 | 6 | 70[h] | Catalyst complex XIVb | 0.1 | | | 1.2 | | 94.2 | 30.1 | 37.2 | 31.6 |
| 20[d] | 155 | 12 | 1.5 | 11 | Catalyst complex XIVb | 0.1 | | | 1.1 | | 81.6 | 35.4 | 9 | 51 |
| 21[d] | 155 | 12 | 6 | 70[n] | [RuHCl(CO)(PPh$_3$)$_3$] | 0.1 | Triphos[f] | 0.1 | 3.4 | | 19.8 | 95.4 | 0 | 1.5 |
| 22[d] | 155 | 12 | 6 | 38 | [RuHCl(CO)(PPh$_3$)$_3$] | 0.2 | DPPEPP | 0.2 | 1.0 | | 66.6 | 68.1 | 0.1 | 11 |
| 23[d][o] | 155 | 12 | 6 | 41 | [RuHCl(CO)(PPh$_3$)$_3$] | 0.2 | DPPEPP | 0.2 | 4.3 | | 39.4 | 56.2 | 0 | 4.3 |
| 24[d] | 180 | 12 | 6 | 82[n] | Catalyst complex XIVb | 0.1 | | | 2.3 | | 89.9 | 36.2 | 35.4 | 27.7 |

[a] 50 ml of toluene; batch size: 25 mmol of 1,4-butanediol,
[b] Evaluation by means of GC (area %);
[c] Product selectivity determined by means of GC;
[d] Ru partition coefficient was determined by reference to the measured Ru contents in 50 ml of organic solvent and 5 ml of water (addition after the end of the reaction);
[e] Molar equivalents of NH$_3$ per OH function on the substrate;
[f] Triphos = 1,1,1-tris(diphenylphosphinomethyl)ethane, CAS 22031-12-5;
[g] Xantphos = 4,5-bis(diphenylphosphino)-9,9-dimethylxanthene, CAS 161265-03-8;
[h] 5 bar H$_2$ injected cold;
[i] 20 bar H$_2$ injected cold;
[j] 30 bar H$_2$ injected cold;
[k] Ru partition coefficient was determined by reference to the measured Ru contents in 50 ml of organic solvent and 50 ml of water (addition after the end of the reaction),
[l] Tetraphos = tris[2-(diphenylphosphino)ethyl]phosphine, CAS 23582-03-8,
[m] 5 mol % water per OH function on the substrate,
[n] 10 bar H$_2$ injected cold,
[o] 0.2 mol % potassium tert-butanolate,
[p] Bis(2-diphenylphosphinoethyl)phenylphosphine, CAS: 23582-02-7
[q] P$_{MC}$ = mRu (upper phase)/mRu (lower phase); P$_C$ = cRu (upper phase)/cRu (lower phase);
[r] mol % based on number of OH functions on the substrate

TABLE 2

Reaction of diethylene glycol

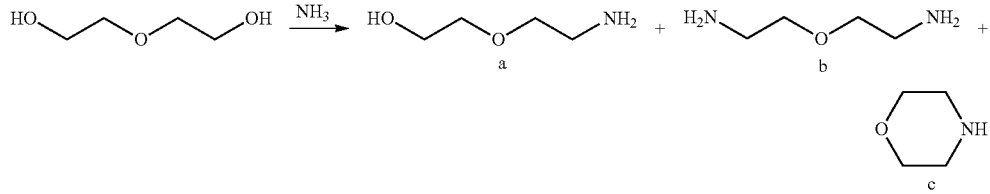

| No.[a] | T (°C.) | Time (h) | Reaction pressure [bar] | Metal salt | Metal [M] (mol %)[h] | Ligand [L] | Ligand (mol %)[h] | $P_C$ (m) (Ru)[e] | $P_C$ (c) (Ru)[e] | Conversion[b] | Selectivity[c] a : | b : | c |
|---|---|---|---|---|---|---|---|---|---|---|---|---|---|
| 1[d] | 155 | 12 | 59[k] | [RuHCl(CO)(PPh$_3$)$_3$] | 0.1 | Triphos[f] | 0.1 | 2.5 | | 16.2 | 87.3 | 0.1 | 2.3 |
| 2[d] | 135 | 12 | 37 | Catalyst complex XIVb | 0.1 | | | 3.3 | | 42.1 | 87.1 | 3.3 | 6.5 |
| 3[d] | 155 | 12 | 43 | Catalyst complex XIVb | 0.1 | | | 1.7 | | 82.4 | 55.3 | 20.1 | 10.9 |
| 4[d] | 180 | 12 | 87[m] | [RuHCl(CO)(PPh$_3$)$_3$] | 0.2 | Triphos[f] | 0.2 | 15.6 | 2.3 | 24.1 | 93.0 | 1.2 | 5.3 |
| 5[g] | 155 | 12 | 67[l] | Catalyst complex XIVb | 0.1 | | | 1.9 | 2.0 | 12.2 | 94.1 | 2.1 | 2.0 |
| 6[g] | 155 | 12 | 82[m] | Catalyst complex XIVb | 0.1 | | | 5.9 | 6.1 | 4.2 | 93.3 | 0 | 2.1 |
| 7[g] | 155 | 12 | 94[n] | Catalyst complex XIVb | 0.1 | | | 5.4 | 5.7 | 2.2 | 91.9 | 0 | 0 |
| 8[g] | 155 | 12 | 43 | Catalyst complex XIVb | 0.1 | | | 1.9 | 2.0 | 79.6 | 57.6 | 22.4 | 12.8 |
| 9[d] | 155 | 12 | 42.6 | [RuHCl(CO)(PPh$_3$)$_3$] | 0.10 | Xanthphos[i] | 0.10 | 1.1 | | 27.7 | 67.1 | 0.2 | 5.26 |
| 10[d)o] | 155 | 15 | 46.4 | Catalyst complex XIVb | 0.10 | | | 1.1 | | 77.5 | 49.1 | 23.7 | 13.08 |
| 11[d] | 155 | 12 | 41.8 | [RuHCl(CO)(PPh$_3$)$_3$] | 0.10 | Triphos[f] | 0.10 | 1.0 | | 52.4 | 66.2 | 0.9 | 6.60 |
| 12[d] | 155 | 12 | 61.2[k] | [RuHCl(CO)(PPh$_3$)$_3$] | 0.10 | Xanthphos[i] | 0.10 | 1.2 | | 19.0 | 75.0 | 0.1 | 5.85 |
| 13[d] | 155 | 12 | 57.1[k] | Catalyst complex XIVb | 0.10 | | | 1.3 | | 29.4 | 87.0 | 6.7 | 3.58 |
| 14[d] | 180 | 12 | 64.7 | [RuHCl(CO)(PPh$_3$)$_3$] | 0.20 | Triphos[f] | 0.20 | 2.0 | | 97.6 | 26.4 | 13.4 | 53.98 |
| 15[d)q] | 155 | 12 | 7.5 | Catalyst complex XIVb | 0.10 | | | 1.4 | | 85.9 | 18.4 | 7.5 | 41.55 |
| 16[d] | 155 | 12 | 58.8 | [RuHCl(CO)(PPh$_3$)$_3$] | 0.40 | Triphos[f] | 0.40 | 1.1 | | 64.7 | 65.2 | 1.3 | 17.97 |
| 17[d] | 180 | 12 | 61.1[k] | [RuHCl(CO)(PPh$_3$)$_3$] | 0.20 | Triphos[f] | 0.20 | 1.7 | | 93.0 | 43.7 | 11.6 | 38.76 |
| 18[d] | 180 | 12 | 60.6[k] | [RuHCl(CO)(PPh$_3$)$_3$] | 0.40 | Triphos[f] | 0.40 | 2.4 | | 95.3 | 38.0 | 9.8 | 48.00 |
| 19[d] | 155 | 60 | 60.1[k] | [RuHCl(CO)(PPh$_3$)$_3$] | 0.20 | Triphos[f] | 0.20 | 6.0 | | 86.1 | 52.4 | 6.9 | 35.35 |
| 20[d] | 155 | 60 | 58.8[k] | [RuHCl(CO)(PPh$_3$)$_3$] | 0.10 | Triphos[f] | 0.10 | 3.4 | | 85.1 | 52.8 | 8.3 | 31.65 |
| 21[d)p] | 155 | 12 | 42.2 | [RuHCl(CO)(PPh$_3$)$_3$] | 0.20 | DPPEPP[j] | 0.20 | 2.0 | | 23.1 | 46.9 | 0.0 | 5.51 |
| 22[d] | 180 | 12 | 75.6[l] | Catalyst complex XIVb | 0.10 | | | 2.3 | | 86.1 | 35.7 | 47.2 | 13.77 |
| 23[d] | 180 | 12 | 95.9[m] | Catalyst complex XIVb | 0.10 | | | 3.4 | | 29.1 | 71.8 | 18.2 | 5.32 |
| 24[d] | 180 | 12 | 79.7[l] | [RuHCl(CO) (PPh$_3$)$_3$] | 0.20 | Triphos[f] | 0.20 | 6.39 | | 54.1 | 83.5 | 3.3 | 11.96 |

[a] 50 ml of toluene; batch size: 25 mmol of diethylene glycol, 6 molar equivalents of NH$_3$ per OH function on the substrate (unless stated otherwise)

[b] Evaluation by means of GC (area %);

[c] Product selectivity determined by means of GC;

[d] Ru partition coefficient was determined by reference to the measured Ru contents in 50 ml of organic solvent and 5 ml of water (addition after the end of the reaction);

[e] $P_{MC}$ = mRu (upper phase)/mRu (lower phase); $P_C$ = cRu (upper phase)/cRu (lower phase);

[f] Triphos = 1,1,1-tris(diphenylphosphinomethyl)ethane, CAS 22031-12-5;

[g] Ru partition coefficient was determined by reference to the measured Ru contents in 50 ml of organic solvent and 50 ml of water (addition after the end of the reaction),

[h] mol % based on number of OH functions on the substrate,

[i] Xantphos = 4,5-bis(diphenylphosphino)-9,9-dimethylxanthene, CAS 161265-03-8;

[j] Bis(2-diphenylphosphinoethyl)phenylphosphine, CAS: 23582-02-7

[k] 5 bar H$_2$ injected cold;

[l] 10 bar H$_2$ injected cold;

[m] 20 bar H$_2$ injected cold;

[n] 30 bar H$_2$ injected cold;

[o] 5 mol % water per OH function on the substrate,

[p] 0.2 mol % potassium tert-butanolate,

[q] Only 1 molar equivalent of NH$_3$ per OH function on the substrate

TABLE 3

Reaction of MEG

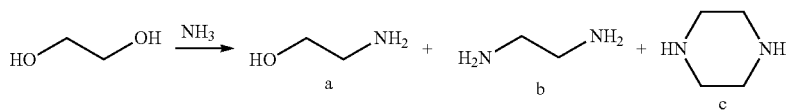

| No.[a] | T (° C.) | Time (h) | Reaction pressure [bar] | Further conditions[g] | Metal salt | Metal [M] (mol %)[g] | Ligand [L][h] | Ligand (mol %)[g] | $P_C$(m) (Ru)[d,e] | $P_C$(c) (Ru)[d,f] | Conversion[b] | Selectivity[c] a : | b : | c |
|---|---|---|---|---|---|---|---|---|---|---|---|---|---|---|
| 1 | 180 | 12 | 36 | | [RuHCl(CO)(PPh$_3$)$_3$] | 0.20 | Triphos | 0.20 | 20.4 | 2.6 | 45.2 | 8.8 | 1.5 | 59.9 |
| 2 | 155 | 12 | 42 | | [RuHCl(CO)(PPh$_3$)$_3$] | 0.20 | Triphos | 0.20 | 13.3 | 1.7 | 20.8 | 23.2 | 3.6 | 40.4 |
| 3 | 155 | 12 | 57 | | [RuHCl(CO)(PPh$_3$)$_3$] | 0.20 | Triphos | 0.20 | 21.0 | 2.7 | 19.9 | 25.1 | 3.4 | 34.4 |
| 4 | 155 | 12 | 57 | | [RuHCl(CO)(PPh$_3$)$_3$] | 0.40 | Triphos | 0.40 | 14.4 | 1.8 | 34.3 | 19.9 | 2.8 | 15.3 |
| 5 | 180 | 12 | 48 | 1 mol % KOtBu | [RuHCl(CO)(PPh$_3$)$_3$] | 0.20 | Triphos | 0.20 | 19.4 | 2.5 | 43.8 | 34.0 | 13.0 | 20.6 |
| 6 | 155 | 12 | 42 | 1 mol % KOtBu | [RuHCl(CO)(PPh$_3$)$_3$] | 0.20 | Triphos | 0.20 | 9.3 | 1.2 | 20.0 | 50.5 | 11.1 | 6.9 |
| 7 | 180 | 12 | 47 | Inject 5 bar H$_2$ cold | [RuHCl(CO)(PPh$_3$)$_3$] | 0.20 | Triphos | 0.20 | 8.0 | 1.0 | 41.2 | 10.3 | 2.8 | 57.0 |
| 8 | 155 | 12 | 42 | Inject 5 bar H$_2$ cold | [RuHCl(CO)(PPh$_3$)$_3$] | 0.20 | Triphos | 0.20 | 19.9 | 2.6 | 21.6 | 22.2 | 3.5 | 33.9 |
| 9 | 180 | 12 | 51 | 5 mol % H$_2$O | [RuHCl(CO)(PPh$_3$)$_3$] | 0.20 | Triphos | 0.20 | 11.9 | 1.5 | 39.3 | 11.1 | 3.01 | 54.6 |
| 10 | 155 | 12 | 40 | 5 mol % H$_2$O | [RuHCl(CO)(PPh$_3$)$_3$] | 0.20 | Triphos | 0.20 | 17.7 | 2.3 | 19.6 | 21.7 | 3.1 | 33.5 |
| 11 | 155 | 60 | 57 | Inject 5 bar H$_2$ cold | [RuHCl(CO)(PPh$_3$)$_3$] | 0.20 | Triphos | 0.20 | 63.9 | 8.2 | 57.6 | 14.0 | 5.4 | 62.1 |
| 12 | 155 | 60 | 57 | Inject 5 bar H$_2$ cold | [RuHCl(CO)(PPh$_3$)$_3$] | 0.10 | Triphos | 0.10 | 24.9 | 3.2 | 35.0 | 15.7 | 7.1 | 63.6 |

[a] 50 ml of toluene; batch size: 25 mmol of ethylene glycol, 6 molar equivalents of NH$_3$ per OH function on the substrate;
[b] evaluation by means of GC (area %);
[c] product selectivity determined by means of GC;
[d] Ru partition coefficient was determined by reference to the measured Ru contents in 50 ml of organic solvent and 5 ml of water;
[e] $P_c$(m) = $m_{Ru}$ (upper phase)/$m_{Ru}$ (lower phase);
[f] $P_c$(c) = $c_{Ru}$ (upper phase)/$c_{Ru}$ (lower phase);
[g] mol % based on number of OH functions on the substrate;
[h] Triphos = 1,1,1-tris(diphenylphosphinomethyl)ethane, CAS 22031-12-5

The invention claimed is:

1. A process for the preparation of primary amines by alcohol amination of alcohols with ammonia with elimination of water, the process comprising
   (a) homogeneously catalytically reacting a mixture comprising an alcohol, ammonia, and a nonpolar solvent in the presence of a catalyst comprising at least one element selected from groups 8, 9 and 10 of the Periodic Table of the Elements, in a liquid phase, to obtain a product mixture P,
   (b) phase separating the product mixture P, optionally after performing at least one operation selected from the group consisting of lowering the temperature, lowering the pressure, and adding at least one polar solvent having a miscibility gap with the nonpolar solvent, to obtain at least one polar product phase A and at least one nonpolar phase B comprising at least some of the catalyst used, and separating off the nonpolar phase B,
   (c) returning at least some of the nonpolar phase B to the mixture in (a), and
   (d) separating off an amination product from the polar product phase A,
   where the nonpolar solvent used in (a) and the catalyst used in (a) are such that the catalyst accumulates in the nonpolar phase B.

2. The process according to claim 1, wherein the amination product comprises an alkanolamine, a diamine, a triamine or a polyamine.

3. The process according to claim 1, wherein the alcohol has at least one primary or secondary alcohol group.

4. The process according to claim 1, wherein the alcohol has at least one primary or secondary alcohol group and at least a second functional group selected from a primary or secondary alcohol group and a primary amino group.

5. The process according to claim 1, wherein (i) the mixture in (a) further comprises a polar solvent, (ii) the phase separating in (b) is after adding at least one polar solvent, or both (i) and (ii), wherein the polar solvent has a miscibility gap with the nonpolar solvent and wherein the amination product has a higher solubility in the polar solvent than in the nonpolar solvent.

6. The process according to claim 1, wherein a quantitative partition coefficient $P_{MC}$=[amount of dissolved catalyst in the nonpolar phase B]/[amount of dissolved catalyst in the polar product phase A] is at least 1.5.

7. The process according to claim 1, wherein a quantitative partition coefficient $P_{MA}$=[amount of amination product in the polar phase A]/[amount of amination product in the nonpolar phase B] is at least 1.5.

8. The process according to claim 1, wherein the polar solvent is at least one selected from the group consisting of water, dimethylformamide, formamide, acetonitrile, and the alcohol of (a).

9. The process according to claim 1, wherein the nonpolar solvent is at least one selected from the group consisting of a saturated hydrocarbon, a linear ether, a cyclic ether, and an aromatic hydrocarbon.

10. The process according to claim 1, wherein, prior to separating off the amination product in (d), catalyst present in the polar product phase A is extracted with the nonpolar solvent used in (a).

11. The process according to claim 10, wherein the extracted catalyst is returned at least partially to the mixture in (a).

12. The process according to claim 1, wherein, in (d), the amination product is separated off from the polar product phase A by distillation.

13. The process according to claim 1, wherein the catalyst comprises Ru, Ir, or both.

14. The process according to claim 1, wherein the catalyst comprises a phosphorus donor ligand.

15. The process according to claim 1, wherein the reacting in (a) is carried out at a temperature of 20 to 250° C. and at a pressure of 0.1 to 20 MPa absolute.

16. The process according to claim 1, wherein the reacting in (a) further comprises adding a base.

17. The process according to claim 1, wherein the alcohol is a diol, a triol, or a polyol.

18. The process according to claim 1, wherein the catalyst comprises Ru.

19. The process according to claim 1, wherein the catalyst comprises Ir.

20. The process of claim 1, wherein the catalyst comprises a phosphorus donor ligand, and Ru or Ir.

* * * * *